(12) United States Patent
Wilt et al.

(10) Patent No.: US 10,201,650 B2
(45) Date of Patent: Feb. 12, 2019

(54) APPARATUS AND METHOD FOR DETECTING DISCONNECTION OF AN INTRAVASCULAR ACCESS DEVICE

(71) Applicant: DEKA Products Limited Partnership, Manchester, NH (US)

(72) Inventors: Michael J. Wilt, Windham, NH (US); Jason M. Sachs, Goffstown, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 1108 days.

(21) Appl. No.: 14/521,654

(22) Filed: Oct. 23, 2014

(65) Prior Publication Data
US 2015/0042366 A1  Feb. 12, 2015

Related U.S. Application Data

(63) Continuation of application No. 12/916,021, filed on Oct. 29, 2010.
(Continued)

(51) Int. Cl.
*A61M 37/00* (2006.01)
*A61M 1/36* (2006.01)
(Continued)

(52) U.S. Cl.
CPC ........ *A61M 1/3656* (2014.02); *A61M 1/3653* (2013.01); *A61M 1/3655* (2013.01);
(Continued)

(58) Field of Classification Search
CPC .............. A61M 1/3659; A61M 1/3653; A61M 1/3655; A61M 1/3656; G01N 27/07; G01R 27/14
See application file for complete search history.

(56) References Cited

U.S. PATENT DOCUMENTS 1,693,526 A   11/1928   Owens
2,529,028 A   11/1950   Landon
(Continued)

FOREIGN PATENT DOCUMENTS

CN   1167430 A   12/1997
CN   2374187 Y   4/2000
(Continued)

OTHER PUBLICATIONS

Office Action for MX Application No. MX/A/2015/001507 filed Jan. 30, 2015, which Office Action is dated Feb. 28, 2017, and claims as pending for MX Application No. MX/A/2015/001507 as of Feb. 28, 2017.
(Continued)

*Primary Examiner* — Ariana Zimbouski
(74) *Attorney, Agent, or Firm* — Wolf, Greenfield & Sacks, P.C.

(57) ABSTRACT

An apparatus and method are disclosed for detecting the disconnection of a vascular access device such as a needle, cannula or catheter from a blood vessel or vascular graft segment. A pair of electrodes is placed in direct contact with fluid or blood in fluid communication with the vascular segment. In one embodiment, the electrodes are incorporated into a pair of connectors connecting arterial and venous catheters to arterial and venous tubes leading to and from an extracorporeal blood flow apparatus. Wires leading from the electrodes to a detecting circuit can be incorporated into a pair of double lumen arterial and venous tubes connecting the blood flow apparatus to the blood vessel or vascular graft. The detecting circuit is configured to provide a low-voltage alternating current signal to the electrodes to measure the electrical resistance between the electrodes, minimizing both the duration and amount of current being delivered. Detection of an increase in electrical resistance
(Continued)

between the electrodes exceeding a pre-determined threshold value may be used to indicate a possible disconnection of the vascular access device.

8 Claims, 13 Drawing Sheets

Related U.S. Application Data

(60) Provisional application No. 61/256,735, filed on Oct. 30, 2009.

(51) Int. Cl.
  *G01N 27/07* (2006.01)
  *G01R 27/14* (2006.01)

(52) U.S. Cl.
  CPC .......... *A61M 1/3659* (2014.02); *G01N 27/07* (2013.01); *G01R 27/14* (2013.01); *A61M 2205/3317* (2013.01)

(56) References Cited

U.S. PATENT DOCUMENTS

| | | |
|---|---|---|
| 2,741,099 A | 4/1956 | Beane |
| 2,816,514 A | 12/1957 | Freese |
| 3,016,563 A | 1/1962 | De Jong |
| 3,200,648 A | 8/1965 | Waggaman |
| 3,508,656 A | 4/1970 | Serfass et al. |
| 3,539,081 A | 11/1970 | Norton et al. |
| 3,656,873 A | 4/1972 | Schiff |
| 3,759,483 A | 9/1973 | Baxter |
| RE27,849 E | 12/1973 | Wortman |
| 3,827,561 A | 8/1974 | Serfass et al. |
| 3,847,809 A | 11/1974 | Kopf |
| 3,882,861 A | 5/1975 | Kettering et al. |
| 3,908,441 A | 9/1975 | Virloget |
| 3,936,729 A | 2/1976 | Winslow |
| 4,085,047 A | 4/1978 | Thompson |
| 4,096,211 A | 6/1978 | Rameau |
| 4,096,859 A | 6/1978 | Agarwal et al. |
| 4,133,312 A | 1/1979 | Burd |
| 4,155,852 A | 5/1979 | Fischel et al. |
| 4,161,264 A | 7/1979 | Malmgren et al. |
| 4,181,610 A | 1/1980 | Shintani et al. |
| 4,227,814 A | 10/1980 | Soodak et al. |
| 4,266,814 A | 5/1981 | Gallagher |
| 4,267,040 A | 5/1981 | Schal et al. |
| 4,282,099 A | 8/1981 | Jones |
| 4,299,784 A | 11/1981 | Hense |
| 4,309,592 A | 1/1982 | Le Boeuf |
| 4,322,054 A | 3/1982 | Campbell |
| 4,362,156 A | 12/1982 | Feller et al. |
| 4,369,781 A | 1/1983 | Gilson et al. |
| 4,398,908 A | 8/1983 | Siposs |
| 4,411,783 A | 10/1983 | Dickens et al. |
| 4,439,188 A | 3/1984 | Dennehy et al. |
| 4,441,357 A | 4/1984 | Kahn et al. |
| 4,479,760 A | 10/1984 | Bilstad et al. |
| 4,479,761 A | 10/1984 | Bilstad et al. |
| 4,479,762 A | 10/1984 | Bilstad et al. |
| 4,490,254 A | 12/1984 | Gordon et al. |
| 4,492,258 A | 1/1985 | Lichtenstein et al. |
| 4,501,405 A | 2/1985 | Usry |
| 4,574,876 A | 3/1986 | Aid |
| 4,585,442 A | 4/1986 | Marines |
| 4,623,334 A | 11/1986 | Riddell |
| 4,623,450 A | 11/1986 | Vantard et al. |
| 4,656,427 A | 4/1987 | Dauphinee et al. |
| 4,664,891 A | 5/1987 | Cosentino et al. |
| 4,680,445 A | 7/1987 | Ogawa |
| 4,695,385 A | 9/1987 | Boag |
| 4,718,022 A | 1/1988 | Cochran |
| 4,731,072 A | 3/1988 | Aid |
| 4,745,279 A | 5/1988 | Karkar et al. |
| 4,767,526 A | 8/1988 | Vantard |
| 4,770,769 A | 9/1988 | Schael et al. |
| 4,778,451 A | 10/1988 | Kamen |
| 4,784,495 A | 11/1988 | Jonsson et al. |
| 4,808,161 A | 2/1989 | Kamen |
| 4,822,343 A | 4/1989 | Beiser |
| 4,826,482 A | 5/1989 | Kamen |
| 4,828,543 A | 5/1989 | Weiss et al. |
| 4,829,448 A | 5/1989 | Balding et al. |
| 4,833,329 A | 5/1989 | Quint et al. |
| 4,863,461 A | 9/1989 | Jarvik |
| 4,884,065 A | 11/1989 | Crouse et al. |
| 4,906,816 A | 3/1990 | van Leerdam |
| 4,927,411 A | 5/1990 | Pastrone et al. |
| 4,950,235 A | 8/1990 | Slate et al. |
| 4,971,700 A | 11/1990 | Tsuji et al. |
| 4,976,162 A | 12/1990 | Kamen |
| 4,976,729 A | 12/1990 | Holfert et al. |
| 4,997,570 A | 3/1991 | Polaschegg |
| 5,024,756 A | 6/1991 | Sternby |
| 5,033,513 A | 7/1991 | Bartholomew |
| 5,061,241 A | 10/1991 | Stephens, Jr. et al. |
| 5,062,774 A | 11/1991 | Kramer et al. |
| 5,074,838 A | 12/1991 | Kroyer |
| 5,088,515 A | 2/1992 | Kamen |
| 5,088,901 A | 2/1992 | Brauer |
| 5,100,554 A | 3/1992 | Polaschegg |
| 5,105,981 A | 4/1992 | Gehman |
| 5,110,447 A | 5/1992 | MacWilliams et al. |
| 5,110,477 A | 5/1992 | Howard et al. |
| 5,116,316 A | 5/1992 | Sertic et al. |
| 5,125,069 A | 6/1992 | O'Boyle |
| 5,160,325 A | 11/1992 | Nichols et al. |
| 5,178,182 A | 1/1993 | Kamen |
| 5,245,693 A | 9/1993 | Ford et al. |
| 5,247,434 A | 9/1993 | Peterson et al. |
| 5,267,956 A | 12/1993 | Beauchat |
| 5,278,072 A | 1/1994 | Wall et al. |
| 5,300,044 A | 4/1994 | Classey et al. |
| 5,306,242 A | 4/1994 | Joyce et al. |
| 5,324,422 A | 6/1994 | Colleran et al. |
| 5,326,476 A | 7/1994 | Grogan et al. |
| D350,823 S | 9/1994 | Lanigan |
| D350,850 S | 9/1994 | Angelini |
| 5,349,896 A | 9/1994 | Delaney, III et al. |
| 5,350,357 A | 9/1994 | Kamen et al. |
| 5,351,686 A | 10/1994 | Steuer et al. |
| 5,378,126 A | 1/1995 | Abrahamson et al. |
| 5,381,510 A | 1/1995 | Ford et al. |
| 5,385,540 A | 1/1995 | Abbott et al. |
| 5,395,316 A | 3/1995 | Martin |
| 5,410,255 A | 4/1995 | Bailey |
| 5,411,472 A | 5/1995 | Steg, Jr. et al. |
| 5,413,566 A | 5/1995 | Sevrain et al. |
| 5,420,962 A | 5/1995 | Bakke |
| 5,421,823 A | 6/1995 | Kamen et al. |
| 5,423,738 A | 6/1995 | Robinson et al. |
| 5,429,485 A | 7/1995 | Dodge |
| 5,431,626 A | 7/1995 | Bryant et al. |
| 5,438,510 A | 8/1995 | Bryant et al. |
| 5,441,231 A | 8/1995 | Payne et al. |
| 5,441,343 A | 8/1995 | Pylkki et al. |
| 5,441,636 A | 8/1995 | Chevallet et al. |
| 5,469,070 A | 11/1995 | Koluvek |
| 5,472,614 A | 12/1995 | Rossi |
| 5,474,683 A | 12/1995 | Bryant et al. |
| 5,476,368 A | 12/1995 | Rabenau et al. |
| 5,476,444 A | 12/1995 | Keeling et al. |
| 5,482,440 A | 1/1996 | Dennehey et al. |
| 5,486,286 A | 1/1996 | Peterson et al. |
| 5,487,827 A | 1/1996 | Peterson et al. |
| 5,496,273 A | 3/1996 | Pastrone et al. |
| 5,527,507 A | 6/1996 | Childers et al. |
| 5,541,344 A | 7/1996 | Becker et al. |
| 5,542,919 A | 8/1996 | Simon et al. |
| 5,558,255 A | 9/1996 | Sancoff et al. |
| 5,568,362 A | 10/1996 | Hansson |
| 5,575,310 A | 11/1996 | Kamen et al. |

(56) References Cited

U.S. PATENT DOCUMENTS

| | | |
|---|---|---|
| 5,578,012 A | 11/1996 | Kamen et al. |
| 5,580,460 A | 12/1996 | Polaschegg et al. |
| 5,586,438 A | 12/1996 | Fahy et al. |
| 5,591,344 A | 1/1997 | Kenley et al. |
| 5,591,389 A | 1/1997 | Esrock |
| 5,593,290 A | 1/1997 | Greisch et al. |
| 5,601,080 A | 2/1997 | Oppenheimer |
| 5,609,572 A | 3/1997 | Lang |
| 5,628,908 A | 5/1997 | Kamen et al. |
| 5,632,894 A | 5/1997 | White et al. |
| 5,634,896 A | 6/1997 | Bryant et al. |
| 5,645,531 A | 7/1997 | Thompson et al. |
| 5,651,765 A | 7/1997 | Haworth et al. |
| 5,651,893 A | 7/1997 | Kenley et al. |
| 5,651,898 A | 7/1997 | Imura |
| 5,680,111 A | 10/1997 | Danby et al. |
| 5,690,831 A | 11/1997 | Kenley et al. |
| 5,692,729 A | 12/1997 | Harhen |
| 5,702,597 A | 12/1997 | Chevallet et al. |
| 5,729,653 A | 3/1998 | Magliochetti et al. |
| 5,730,720 A | 3/1998 | Sites et al. |
| 5,734,464 A | 3/1998 | Gibbs |
| 5,744,027 A | 4/1998 | Connell et al. |
| 5,755,275 A | 5/1998 | Rose et al. |
| 5,755,683 A | 5/1998 | Houle et al. |
| 5,776,091 A | 7/1998 | Brugger et al. |
| 5,782,508 A | 7/1998 | Bartholomew |
| 5,797,897 A | 8/1998 | Jepson et al. |
| 5,804,979 A | 9/1998 | Lund et al. |
| 5,857,379 A | 1/1999 | Lulofs et al. |
| 5,875,282 A | 2/1999 | Jordan et al. |
| 5,879,316 A | 3/1999 | Safar et al. |
| 5,882,047 A | 3/1999 | Ostrander et al. |
| 5,899,873 A | 5/1999 | Jones et al. |
| 5,902,476 A | 5/1999 | Twardowski et al. |
| 5,931,648 A | 8/1999 | Del Canizo |
| 5,932,103 A | 8/1999 | Kenley et al. |
| 5,932,110 A | 8/1999 | Shah et al. |
| 5,938,634 A | 8/1999 | Packard |
| 5,947,931 A | 9/1999 | Bierman et al. |
| 5,989,423 A | 11/1999 | Kamen et al. |
| 6,039,877 A | 3/2000 | Chevallet et al. |
| 6,041,801 A | 3/2000 | Gray et al. |
| 6,042,784 A | 3/2000 | Wamsiedler et al. |
| 6,044,868 A | 4/2000 | Gretz et al. |
| 6,047,108 A | 4/2000 | Sword et al. |
| 6,062,068 A | 5/2000 | Bowling et al. |
| 6,070,761 A | 6/2000 | Bloom et al. |
| 6,089,105 A | 7/2000 | Ricciardelli |
| 6,101,406 A | 8/2000 | Hacker et al. |
| 6,109,881 A | 8/2000 | Snodgrass et al. |
| 6,136,201 A | 10/2000 | Shah et al. |
| 6,139,534 A | 10/2000 | Niedospial, Jr. et al. |
| 6,139,819 A | 10/2000 | Unger et al. |
| 6,142,164 A | 11/2000 | Wier et al. |
| 6,142,446 A | 11/2000 | Leinsing |
| 6,146,354 A | 11/2000 | Beil |
| 6,146,523 A | 11/2000 | Kenley et al. |
| 6,146,536 A | 11/2000 | Twardowski |
| 6,153,102 A | 11/2000 | Kenley et al. |
| 6,159,192 A | 12/2000 | Fowles et al. |
| 6,171,261 B1 | 1/2001 | Niermann et al. |
| 6,176,904 B1 | 1/2001 | Gupta |
| 6,195,887 B1 | 3/2001 | Danby et al. |
| 6,210,361 B1 | 4/2001 | Kamen et al. |
| 6,213,996 B1 | 4/2001 | Jepson et al. |
| 6,223,130 B1 | 4/2001 | Gray et al. |
| 6,234,997 B1 | 5/2001 | Kamen et al. |
| 6,264,680 B1 | 7/2001 | Ash |
| RE37,324 E | 8/2001 | Esrock |
| 6,274,303 B1 | 8/2001 | Wowk et al. |
| 6,277,277 B1 | 8/2001 | Jacobi et al. |
| 6,284,131 B1 | 9/2001 | Hogard et al. |
| 6,302,653 B1 | 10/2001 | Bryant et al. |
| 6,321,597 B1 | 11/2001 | Demers et al. |
| 6,331,778 B1 | 12/2001 | Dailey et al. |
| 6,336,003 B1 | 1/2002 | Mitsunaga et al. |
| 6,336,911 B1 | 1/2002 | Westerbeck |
| 6,347,633 B1 | 2/2002 | Groth et al. |
| 6,382,923 B1 | 5/2002 | Gray |
| 6,406,426 B1 | 6/2002 | Reuss et al. |
| 6,406,452 B1 | 6/2002 | Westerbeck |
| 6,413,233 B1 | 7/2002 | Sites et al. |
| 6,415,797 B1 | 7/2002 | Groth et al. |
| 6,416,293 B1 | 7/2002 | Bouchard et al. |
| 6,423,053 B1 | 7/2002 | Lee |
| 6,464,666 B1 | 10/2002 | Augustine et al. |
| 6,480,257 B2 | 11/2002 | Cassidy et al. |
| 6,485,263 B1 | 11/2002 | Bryant et al. |
| 6,491,656 B1 | 12/2002 | Morris |
| 6,497,676 B1 | 12/2002 | Childers et al. |
| 6,510,330 B1 | 1/2003 | Enejder |
| 6,517,510 B1 | 2/2003 | Stewart et al. |
| 6,520,747 B2 | 2/2003 | Gray et al. |
| 6,527,758 B2 | 3/2003 | Ko |
| 6,529,775 B2 | 3/2003 | Whitebook et al. |
| 6,535,689 B2 | 3/2003 | Augustine et al. |
| 6,537,445 B2 | 3/2003 | Muller |
| 6,539,172 B2 | 3/2003 | Akahane |
| 6,543,814 B2 | 4/2003 | Bartholomew |
| 6,579,253 B1 | 6/2003 | Burbank et al. |
| 6,579,496 B1 | 6/2003 | Fausset et al. |
| RE38,203 E | 7/2003 | Kelly |
| 6,595,944 B2 | 7/2003 | Balschat et al. |
| 6,595,948 B2 | 7/2003 | Suzuki et al. |
| 6,604,908 B1 | 8/2003 | Bryant et al. |
| 6,608,968 B2 | 8/2003 | Bakke |
| 6,620,119 B1 | 9/2003 | Utterberg et al. |
| 6,635,491 B1 | 10/2003 | Khalil et al. |
| 6,638,478 B1 | 10/2003 | Treu et al. |
| 6,649,063 B2 | 11/2003 | Brugger et al. |
| 6,660,974 B2 | 12/2003 | Faries, Jr. et al. |
| 6,663,353 B2 | 12/2003 | Lipscomb et al. |
| 6,663,359 B2 | 12/2003 | Gray |
| 6,663,585 B1 * | 12/2003 | Ender .................. A61M 1/367 210/645 |
| 6,673,314 B1 | 1/2004 | Burbank et al. |
| 6,687,004 B1 | 2/2004 | Shana et al. |
| 6,709,417 B1 | 3/2004 | Houle et al. |
| 6,722,865 B2 | 4/2004 | Domroese |
| 6,723,062 B1 | 4/2004 | Westberg et al. |
| 6,726,656 B2 | 4/2004 | Kamen et al. |
| 6,743,201 B1 | 6/2004 | Doing et al. |
| 6,749,403 B2 | 6/2004 | Bryant et al. |
| 6,752,172 B2 | 6/2004 | Lauer |
| 6,758,975 B2 | 7/2004 | Peabody et al. |
| 6,768,085 B2 | 7/2004 | Faries et al. |
| 6,775,473 B2 | 8/2004 | Augustine et al. |
| 6,788,885 B2 | 9/2004 | Mitsunaga et al. |
| 6,808,369 B2 | 10/2004 | Gray et al. |
| 6,814,547 B2 | 11/2004 | Childers et al. |
| 6,814,718 B2 | 11/2004 | McGuckin, Jr. et al. |
| 6,826,948 B1 | 12/2004 | Bhatti et al. |
| 6,852,090 B2 | 2/2005 | Burbank et al. |
| 6,858,019 B2 | 2/2005 | McGuckin, Jr. et al. |
| 6,860,866 B1 | 3/2005 | Graf et al. |
| 6,868,309 B1 | 3/2005 | Begelman |
| 6,877,713 B1 | 4/2005 | Gray et al. |
| 6,905,314 B2 | 6/2005 | Danby |
| 6,905,479 B1 | 6/2005 | Bouchard et al. |
| 6,929,751 B2 | 8/2005 | Bowman et al. |
| 6,939,471 B2 | 9/2005 | Gross et al. |
| 6,946,299 B2 | 9/2005 | Neel et al. |
| 6,949,079 B1 | 9/2005 | Westberg et al. |
| 6,953,323 B2 | 10/2005 | Childers et al. |
| 7,029,245 B2 | 4/2006 | Maianti et al. |
| 7,041,076 B2 | 5/2006 | Westberg et al. |
| 7,060,047 B2 | 6/2006 | Lodi et al. |
| 7,083,719 B2 | 8/2006 | Bowman et al. |
| 7,122,210 B2 | 10/2006 | Elisabettini et al. |
| 7,124,996 B2 | 10/2006 | Clarke et al. |
| 7,138,088 B2 | 11/2006 | Wariar et al. |
| 7,147,613 B2 | 12/2006 | Burbank et al. |
| 7,153,286 B2 | 12/2006 | Busby et al. |

(56) References Cited

U.S. PATENT DOCUMENTS

| | | | |
|---|---|---|---|
| 7,168,334 | B1 | 1/2007 | Drott |
| 7,169,303 | B2 | 1/2007 | Sullivan et al. |
| 7,175,397 | B2 | 2/2007 | Claude et al. |
| 7,175,606 | B2 | 2/2007 | Bowman et al. |
| 7,214,210 | B2 | 5/2007 | Kamen et al. |
| 7,230,687 | B2 | 6/2007 | O'Mahony et al. |
| 7,238,164 | B2 | 7/2007 | Childers et al. |
| 7,273,465 | B2 | 9/2007 | Ash |
| 7,300,413 | B2 | 11/2007 | Burbank et al. |
| 7,303,540 | B2 | 12/2007 | O'Mahony et al. |
| 7,318,292 | B2 | 1/2008 | Helbling et al. |
| 7,318,892 | B2 | 1/2008 | Connell et al. |
| 7,410,294 | B2 | 8/2008 | Shiraki et al. |
| 7,461,968 | B2 | 12/2008 | Demers et al. |
| 7,465,285 | B2 | 12/2008 | Hutchinson et al. |
| 7,476,209 | B2 | 1/2009 | Gara et al. |
| 7,488,448 | B2 | 2/2009 | Wieting et al. |
| 7,500,962 | B2 | 3/2009 | Childers et al. |
| 7,530,962 | B2 | 5/2009 | Ross et al. |
| 7,544,179 | B2 | 6/2009 | Distler et al. |
| 7,559,524 | B2 | 7/2009 | Gray et al. |
| 7,601,636 | B2 | 10/2009 | Dumas et al. |
| 7,632,078 | B2 | 12/2009 | Demers et al. |
| 7,632,080 | B2 | 12/2009 | Tracey et al. |
| 7,644,889 | B2 | 1/2010 | Johnson |
| 7,662,286 | B2 | 2/2010 | Childers et al. |
| 7,699,806 | B2 | 4/2010 | Ware et al. |
| 7,717,682 | B2 | 5/2010 | Orr |
| 7,727,176 | B2 | 6/2010 | Tonelli et al. |
| 7,741,756 | B2 | 6/2010 | Sudol |
| 7,744,553 | B2 | 6/2010 | Kelly et al. |
| 7,776,301 | B2 | 8/2010 | Comrie et al. |
| 7,789,849 | B2 | 9/2010 | Busby et al. |
| 7,794,141 | B2 | 9/2010 | Perry et al. |
| 7,815,595 | B2 | 10/2010 | Busby et al. |
| 7,867,214 | B2 | 1/2011 | Childers et al. |
| 7,892,197 | B2 | 2/2011 | Folden et al. |
| 7,896,830 | B2 | 3/2011 | Gura et al. |
| 7,899,508 | B2 * | 3/2011 | DeArmond ........ A61B 5/02042 600/327 |
| 7,935,074 | B2 | 5/2011 | Plahey et al. |
| 7,935,250 | B2 | 5/2011 | Castellano et al. |
| 7,938,792 | B2 | 5/2011 | Roger et al. |
| 7,967,022 | B2 | 6/2011 | Grant et al. |
| 8,002,726 | B2 | 8/2011 | Karoor et al. |
| 8,042,563 | B2 | 10/2011 | Grant et al. |
| 8,066,671 | B2 | 11/2011 | Busby et al. |
| 8,075,526 | B2 | 12/2011 | Busby et al. |
| 8,137,553 | B2 | 3/2012 | Fulkerson et al. |
| 8,180,443 | B1 | 5/2012 | Kleinekofort et al. |
| 8,246,826 | B2 | 8/2012 | Wilt et al. |
| 8,248,087 | B2 | 8/2012 | Ishino et al. |
| 8,273,049 | B2 | 9/2012 | Demers et al. |
| 8,292,594 | B2 | 10/2012 | Tracey et al. |
| 8,298,152 | B2 | 10/2012 | Konig et al. |
| 8,317,492 | B2 | 11/2012 | Demers et al. |
| 8,357,298 | B2 | 1/2013 | Demers et al. |
| 8,393,690 | B2 | 3/2013 | Grant et al. |
| 8,409,441 | B2 | 4/2013 | Wilt |
| 8,425,471 | B2 | 4/2013 | Grant et al. |
| 8,459,292 | B2 | 6/2013 | Wilt et al. |
| 8,491,184 | B2 | 7/2013 | Kamen et al. |
| 8,499,780 | B2 | 8/2013 | Wilt et al. |
| 8,545,698 | B2 | 10/2013 | Wilt et al. |
| 8,562,834 | B2 | 10/2013 | Kamen et al. |
| 8,708,950 | B2 | 4/2014 | Scarpaci et al. |
| 8,721,879 | B2 | 5/2014 | van der Merwe et al. |
| 8,721,884 | B2 | 5/2014 | Wilt et al. |
| 8,771,508 | B2 | 7/2014 | Grant et al. |
| 8,858,787 | B2 | 10/2014 | Muller et al. |
| 8,863,772 | B2 | 10/2014 | Dale et al. |
| 8,870,549 | B2 | 10/2014 | Tracey et al. |
| 8,888,470 | B2 | 11/2014 | Demers et al. |
| 8,926,294 | B2 | 1/2015 | Demers et al. |
| 8,968,232 | B2 | 3/2015 | Kamen et al. |
| 8,985,133 | B2 | 3/2015 | Grant et al. |
| 8,992,075 | B2 | 3/2015 | Kamen et al. |
| 8,992,189 | B2 | 3/2015 | Wilt et al. |
| 9,028,691 | B2 | 5/2015 | Grant et al. |
| 9,115,708 | B2 | 8/2015 | van der Merwe et al. |
| 9,272,082 | B2 | 3/2016 | Demers et al. |
| 9,302,037 | B2 | 4/2016 | Wilt et al. |
| 9,364,655 | B2 | 6/2016 | Grant et al. |
| 9,366,781 | B2 | 6/2016 | Scarpaci et al. |
| 9,517,295 | B2 | 12/2016 | Wilt et al. |
| 9,535,021 | B2 | 1/2017 | Kamen et al. |
| 9,539,379 | B2 | 1/2017 | Grant et al. |
| 9,550,018 | B2 | 1/2017 | Demers et al. |
| 9,555,179 | B2 | 1/2017 | Wilt et al. |
| 9,597,442 | B2 | 3/2017 | Wilt |
| 9,603,985 | B2 | 3/2017 | Wilt et al. |
| 9,649,418 | B2 | 5/2017 | Demers et al. |
| 9,677,554 | B2 | 6/2017 | Wilt et al. |
| 9,700,660 | B2 | 7/2017 | Demers et al. |
| 9,700,711 | B2 | 7/2017 | Grant et al. |
| 9,717,834 | B2 | 8/2017 | Wilt et al. |
| 9,724,458 | B2 | 8/2017 | Grant et al. |
| 9,795,728 | B2 | 10/2017 | Grant et al. |
| 9,951,768 | B2 | 4/2018 | Grant et al. |
| 9,987,407 | B2 | 6/2018 | Grant et al. |
| 9,999,717 | B2 | 6/2018 | van der Merwe et al. |
| 2002/0000871 | A1 * | 1/2002 | Davies ............... G11C 16/12 327/540 |
| 2002/0056672 | A1 | 5/2002 | Guy et al. |
| 2002/0092103 | A1 | 7/2002 | Bruno et al. |
| 2002/0103453 | A1 | 8/2002 | Burbank et al. |
| 2002/0150476 | A1 | 10/2002 | Lucke et al. |
| 2002/0179505 | A1 | 12/2002 | Rovatti et al. |
| 2002/0179595 | A1 | 12/2002 | Nagele |
| 2002/0182163 | A1 | 12/2002 | Gray |
| 2003/0036719 | A1 * | 2/2003 | Giacomelli ......... A61M 1/3669 604/5.04 |
| 2003/0100858 | A1 | 5/2003 | Utterberg et al. |
| 2003/0114795 | A1 | 6/2003 | Faries et al. |
| 2003/0194328 | A1 | 10/2003 | Bryant et al. |
| 2003/0194332 | A1 | 10/2003 | Jahn et al. |
| 2003/0195453 | A1 | 10/2003 | Han et al. |
| 2003/0195454 | A1 | 10/2003 | Wariar et al. |
| 2003/0220599 | A1 | 11/2003 | Lundtveit et al. |
| 2003/0220607 | A1 | 11/2003 | Busby et al. |
| 2003/0229302 | A1 | 12/2003 | Robinson et al. |
| 2003/0230191 | A1 | 12/2003 | Ohrle et al. |
| 2004/0001766 | A1 | 1/2004 | Maianti et al. |
| 2004/0009096 | A1 | 1/2004 | Wellman |
| 2004/0019313 | A1 | 1/2004 | Childers et al. |
| 2004/0091374 | A1 | 5/2004 | Gray |
| 2004/0101026 | A1 | 5/2004 | Nitta et al. |
| 2004/0138607 | A1 | 7/2004 | Burbank et al. |
| 2004/0245161 | A1 | 12/2004 | Treu et al. |
| 2004/0262917 | A1 | 12/2004 | Sunohara et al. |
| 2005/0020958 | A1 | 1/2005 | Paolini et al. |
| 2005/0045540 | A1 | 3/2005 | Connell et al. |
| 2005/0069425 | A1 | 3/2005 | Gray et al. |
| 2005/0069427 | A1 | 3/2005 | Roemuss et al. |
| 2005/0095141 | A1 | 5/2005 | Lanigan et al. |
| 2005/0095154 | A1 | 5/2005 | Tracey et al. |
| 2005/0126998 | A1 | 6/2005 | Childers |
| 2005/0130332 | A1 | 6/2005 | Ishii et al. |
| 2005/0131332 | A1 | 6/2005 | Kelly et al. |
| 2005/0195087 | A1 | 9/2005 | Thompson et al. |
| 2005/0209563 | A1 | 9/2005 | Hopping et al. |
| 2005/0230292 | A1 | 10/2005 | Beden et al. |
| 2005/0234385 | A1 | 10/2005 | Vandlik |
| 2005/0242034 | A1 | 11/2005 | Connell et al. |
| 2005/0274658 | A1 | 12/2005 | Rosenbaum et al. |
| 2006/0002823 | A1 | 1/2006 | Feldstein |
| 2006/0093531 | A1 | 5/2006 | Tremoulet et al. |
| 2006/0184084 | A1 | 8/2006 | Ware et al. |
| 2006/0195064 | A1 | 8/2006 | Plahey et al. |
| 2006/0229586 | A1 | 10/2006 | Faries |
| 2006/0241550 | A1 | 10/2006 | Kamen et al. |
| 2007/0060786 | A1 | 3/2007 | Gura et al. |
| 2007/0060872 | A1 | 3/2007 | Hall et al. |
| 2007/0077156 | A1 | 4/2007 | Orr |

(56) References Cited

U.S. PATENT DOCUMENTS

| | | |
|---|---|---|
| 2007/0112297 A1 | 5/2007 | Plahey et al. |
| 2007/0135758 A1 | 6/2007 | Childers et al. |
| 2007/0166181 A1 | 7/2007 | Nilson |
| 2007/0210047 A1 | 9/2007 | Child |
| 2007/0253463 A1 | 11/2007 | Perry et al. |
| 2007/0255527 A1 | 11/2007 | Schick et al. |
| 2007/0278155 A1 | 12/2007 | Lo et al. |
| 2008/0015493 A1 | 1/2008 | Childers et al. |
| 2008/0033346 A1 | 2/2008 | Childers et al. |
| 2008/0058697 A1 | 3/2008 | Kamen et al. |
| 2008/0058712 A1 | 3/2008 | Plahey |
| 2008/0065006 A1 | 3/2008 | Roger et al. |
| 2008/0077068 A1 | 3/2008 | Orr |
| 2008/0097283 A1 | 4/2008 | Plahey |
| 2008/0105600 A1 | 5/2008 | Connell et al. |
| 2008/0125693 A1 | 5/2008 | Connell et al. |
| 2008/0132828 A1 | 6/2008 | Howard |
| 2008/0161751 A1 | 7/2008 | Plahey et al. |
| 2008/0175719 A1 | 7/2008 | Tracey et al. |
| 2008/0202591 A1 | 8/2008 | Grant et al. |
| 2008/0204086 A1 | 8/2008 | Park et al. |
| 2008/0205481 A1 | 8/2008 | Faries, Jr. et al. |
| 2008/0208103 A1 | 8/2008 | Demers et al. |
| 2008/0208111 A1 | 8/2008 | Kamen et al. |
| 2008/0215898 A1 | 9/2008 | Lu et al. |
| 2008/0216898 A1 | 9/2008 | Grant et al. |
| 2008/0240929 A1 | 10/2008 | Kamen et al. |
| 2008/0253427 A1 | 10/2008 | Kamen et al. |
| 2008/0253911 A1 | 10/2008 | Demers et al. |
| 2008/0253912 A1 | 10/2008 | Demers et al. |
| 2008/0287854 A1 | 11/2008 | Sun |
| 2009/0004033 A1 | 1/2009 | Demers et al. |
| 2009/0007642 A1 | 1/2009 | Busby et al. |
| 2009/0008331 A1 | 1/2009 | Wilt et al. |
| 2009/0009290 A1 | 1/2009 | Kneip et al. |
| 2009/0012447 A1 | 1/2009 | Huitt et al. |
| 2009/0012448 A1 | 1/2009 | Childers et al. |
| 2009/0012449 A1 | 1/2009 | Lee et al. |
| 2009/0012450 A1 | 1/2009 | Childers et al. |
| 2009/0012452 A1 | 1/2009 | Slepicka et al. |
| 2009/0012453 A1 | 1/2009 | Childers et al. |
| 2009/0012454 A1 | 1/2009 | Childers |
| 2009/0012455 A1 | 1/2009 | Childers et al. |
| 2009/0012456 A1 | 1/2009 | Childers et al. |
| 2009/0012457 A1 | 1/2009 | Childers et al. |
| 2009/0012458 A1 | 1/2009 | Childers et al. |
| 2009/0012460 A1 | 1/2009 | Steck et al. |
| 2009/0012461 A1 | 1/2009 | Childers et al. |
| 2009/0024070 A1 | 1/2009 | Gelfand et al. |
| 2009/0043239 A1 | 2/2009 | Gagel et al. |
| 2009/0076433 A1 | 3/2009 | Folden et al. |
| 2009/0076434 A1 | 3/2009 | Mischelevich et al. |
| 2009/0088675 A1 | 4/2009 | Kelly et al. |
| 2009/0088683 A1 | 4/2009 | Roger et al. |
| 2009/0095679 A1 | 4/2009 | Demers et al. |
| 2009/0101549 A1 | 4/2009 | Kamen et al. |
| 2009/0101550 A1 | 4/2009 | Muller et al. |
| 2009/0101566 A1 | 4/2009 | Crnkovich et al. |
| 2009/0105621 A1 | 4/2009 | Boyd et al. |
| 2009/0105629 A1 | 4/2009 | Grant et al. |
| 2009/0107335 A1 | 4/2009 | Wilt et al. |
| 2009/0107902 A1 | 4/2009 | Childers et al. |
| 2009/0112151 A1 | 4/2009 | Chapman et al. |
| 2009/0113335 A1 | 4/2009 | Sandoe et al. |
| 2009/0114582 A1 | 5/2009 | Grant et al. |
| 2009/0154524 A1 | 6/2009 | Girelli |
| 2009/0173682 A1 | 7/2009 | Robinson et al. |
| 2009/0182263 A1 | 7/2009 | Burbank et al. |
| 2009/0192367 A1 | 7/2009 | Braig et al. |
| 2009/0202367 A1 | 8/2009 | Gray et al. |
| 2010/0018317 A1 | 1/2010 | Kitani et al. |
| 2010/0051529 A1 | 3/2010 | Grant et al. |
| 2010/0051551 A1 | 3/2010 | Grant et al. |
| 2010/0056975 A1 | 3/2010 | Dale et al. |
| 2010/0057016 A1 | 3/2010 | Dale et al. |
| 2010/0087777 A1 | 4/2010 | Hopping et al. |
| 2010/0133153 A1 | 6/2010 | Beden et al. |
| 2010/0137782 A1 | 6/2010 | Jansson et al. |
| 2010/0185134 A1 | 7/2010 | Houwen et al. |
| 2010/0187176 A1 | 7/2010 | Lopez et al. |
| 2010/0190204 A1 | 7/2010 | Gazenko |
| 2010/0192686 A1 | 8/2010 | Kamen et al. |
| 2010/0204765 A1 | 8/2010 | Hall et al. |
| 2010/0296953 A1 | 11/2010 | Gray |
| 2010/0327849 A1 | 12/2010 | Kamen et al. |
| 2011/0009797 A1 | 1/2011 | Kelly et al. |
| 2011/0092875 A1 | 4/2011 | Beck et al. |
| 2011/0105877 A1 | 5/2011 | Wilt et al. |
| 2011/0144569 A1 | 6/2011 | Britton et al. |
| 2011/0218600 A1 | 9/2011 | Kamen et al. |
| 2011/0299358 A1 | 12/2011 | Wilt et al. |
| 2011/0303588 A1 | 12/2011 | Kelly et al. |
| 2011/0303598 A1 | 12/2011 | Lo et al. |
| 2012/0035533 A1 | 2/2012 | Britton et al. |
| 2012/0071816 A1 | 3/2012 | Busby et al. |
| 2012/0106289 A1 | 5/2012 | Wilt et al. |
| 2012/0123322 A1 | 5/2012 | Scarpaci et al. |
| 2012/0207627 A1 | 8/2012 | Demers et al. |
| 2013/0010825 A1 | 1/2013 | Kamen et al. |
| 2013/0020237 A1 | 1/2013 | Wilt et al. |
| 2013/0022483 A1 | 1/2013 | Wilt et al. |
| 2013/0032536 A1 | 2/2013 | Wilt et al. |
| 2013/0037480 A1 | 2/2013 | Wilt et al. |
| 2013/0037485 A1 | 2/2013 | Wilt et al. |
| 2013/0074959 A1 | 3/2013 | Demers et al. |
| 2013/0115105 A1 | 5/2013 | Tracey et al. |
| 2013/0126413 A1 | 5/2013 | Van der Merwe et al. |
| 2013/0177457 A1 | 7/2013 | Demers et al. |
| 2013/0284648 A1 | 10/2013 | Grant et al. |
| 2013/0304020 A1 | 11/2013 | Wilt et al. |
| 2013/0317454 A1 | 11/2013 | Grant et al. |
| 2014/0102299 A1 | 4/2014 | Wilt et al. |
| 2014/0102958 A1 | 4/2014 | Kamen et al. |
| 2014/0102970 A1 | 4/2014 | Wilt et al. |
| 2014/0112828 A1 | 4/2014 | Grant et al. |
| 2014/0153356 A1 | 6/2014 | Grant et al. |
| 2014/0199193 A1 | 7/2014 | Wilt et al. |
| 2014/0299544 A1 | 10/2014 | Wilt et al. |
| 2014/0309611 A1 | 10/2014 | Wilt et al. |
| 2014/0319041 A1 | 10/2014 | Wilt et al. |
| 2014/0322053 A1 | 10/2014 | van der Merwe et al. |
| 2014/0323954 A1 | 10/2014 | Scarpaci et al. |
| 2015/0042366 A1 | 2/2015 | Wilt et al. |
| 2015/0050166 A1 | 2/2015 | Tracey et al. |
| 2015/0196698 A1 | 7/2015 | Grant et al. |
| 2015/0196699 A9 | 7/2015 | Wilt et al. |
| 2015/0224242 A1 | 8/2015 | Grant et al. |
| 2016/0030658 A1 | 2/2016 | van der Merwe et al. |
| 2016/0058933 A1 | 3/2016 | Ballantyne et al. |
| 2016/0175506 A1 | 6/2016 | Wilt et al. |
| 2017/0000938 A1 | 1/2017 | Wilt et al. |
| 2017/0100533 A1 | 4/2017 | Wilt et al. |
| 2017/0130705 A1 | 5/2017 | Demers et al. |
| 2017/0143886 A1 | 5/2017 | Wilt et al. |
| 2017/0241926 A1 | 8/2017 | Kamen et al. |
| 2017/0252503 A1 | 9/2017 | Wilt |
| 2017/0296803 A1 | 10/2017 | Grant et al. |
| 2017/0319765 A1 | 11/2017 | Wilt et al. |
| 2017/0326282 A1 | 11/2017 | Wilt et al. |
| 2017/0342972 A1 | 11/2017 | Wilt et al. |
| 2017/0368252 A1 | 12/2017 | Grant et al. |
| 2018/0038357 A1 | 2/2018 | Demers et al. |
| 2018/0055984 A1 | 3/2018 | Grant et al. |

FOREIGN PATENT DOCUMENTS

| | | |
|---|---|---|
| CN | 1455262 A | 11/2003 |
| CN | 1830494 A | 9/2006 |
| CN | 101309710 A | 11/2008 |
| CN | 101551354 A | 10/2009 |
| DE | 3 328 744 A1 | 2/1985 |
| DE | 10206666 A1 | 8/2003 |
| EP | 0238809 A2 | 9/1987 |
| EP | 0 687 474 A1 | 12/1995 |

(56) References Cited

FOREIGN PATENT DOCUMENTS

| | | |
|---|---|---|
| EP | 0706044 A1 | 4/1996 |
| EP | 0 815 882 A2 | 1/1998 |
| EP | 0 992 255 A2 | 4/2000 |
| EP | 2 319 551 A2 | 5/2011 |
| GB | 2 423 241 A | 8/2006 |
| JP | S60-077782 U | 5/1985 |
| JP | H09-099060 | 4/1997 |
| JP | H10-319052 A | 12/1998 |
| JP | H11-210633 A | 8/1999 |
| JP | 2001-525229 A | 11/2001 |
| JP | 2006-507024 A | 3/2006 |
| JP | 2006-204343 A | 8/2006 |
| JP | 2008-136673 A | 6/2008 |
| WO | WO 94/20158 A1 | 9/1994 |
| WO | WO 96/40320 A1 | 12/1996 |
| WO | WO 97/09898 A1 | 3/1997 |
| WO | WO 98/37801 A1 | 9/1998 |
| WO | WO 98/39058 A1 | 9/1998 |
| WO | WO 99/10028 A1 | 3/1999 |
| WO | WO 99/29356 | 6/1999 |
| WO | WO 00/15278 A1 | 3/2000 |
| WO | WO 01/37895 A2 | 5/2001 |
| WO | WO 02/03879 A1 | 1/2002 |
| WO | WO 02/30267 A2 | 4/2002 |
| WO | WO 03/080268 A1 | 10/2003 |
| WO | WO 03/086505 | 10/2003 |
| WO | WO 2004/041081 A1 | 5/2004 |
| WO | WO 2005/044339 A1 | 5/2005 |
| WO | WO 2005/044435 A2 | 5/2005 |
| WO | WO 2006/013312 A1 | 2/2006 |
| WO | WO 2006/088419 A2 | 8/2006 |
| WO | WO 2006/120415 A1 | 11/2006 |
| WO | WO 2007/058020 | 5/2007 |
| WO | WO 2007/120812 A2 | 10/2007 |
| WO | WO 2007/126360 A1 | 11/2007 |
| WO | WO 2008/028653 A2 | 3/2008 |
| WO | WO 2008/106191 A2 | 9/2008 |
| WO | WO 2008/106440 A1 | 9/2008 |
| WO | WO 2008/106452 A1 | 9/2008 |
| WO | WO 2008/106538 A2 | 9/2008 |
| WO | WO 2008/118600 A1 | 10/2008 |
| WO | WO 2009/051669 A1 | 4/2009 |
| WO | WO 2009/094179 A2 | 7/2009 |
| WO | WO 2009/094183 A1 | 7/2009 |
| WO | WO 2010/027435 A2 | 3/2010 |
| WO | WO 2010/027437 A2 | 3/2010 |
| WO | WO 2011/053810 A2 | 5/2011 |
| WO | WO 2012/006425 A2 | 1/2012 |

OTHER PUBLICATIONS

Office Action for JP Application No. 2016-198052 filed Oct. 6, 2016, which Office Action is dated Aug. 16, 2017, and claims as pending for JP Application No. 2016-198052.
Office Action for MX Application No. MX/A/2015/001507 filed Jan. 30, 2015, which Office Action is dated Jun. 4, 2015, and claims as pending for MX Application No. MX/A/2015/001507 as of Jun. 4, 2015.
Search Report and Written Opinion for SG Application No. 11201609765V filed May 27, 2015, which Report is dated Nov. 3, 2017, and claims as pending for SG Application No. 11201609765V as of Nov. 3, 2017.
International Search Report and Written Opinion for PCT/US2015/032702 dated Dec. 4, 2015.
International Preliminary Report on Patentability for PCT/US2015/032702 dated Dec. 8, 2016.
Office Action for MX Application No. MX/A/2015/001507 filed Jan. 30, 2015, which Office Action is dated Jun. 3, 2016, and claims as pending for MK Application No. MX/A/2015/001507 as of Jun. 3, 2016.
Office Action for JP Application No. 2009-551724 filed Feb. 27, 2008, which Office Action is dated Nov. 28, 2012, and claims as pending for JP Application No. 2009-551724 as of Nov. 28, 2012.
Written Opinion for Application No. PCT/US2008/002636 dated Jul. 2, 2008.
International Preliminary Report on Patentability for Application No. PCT/US2008/002636 dated Sep. 11, 2009.
International Search Report and Written Opinion for Application No. PCT/US2008/055000 dated Aug. 1, 2008.
International Preliminary Report on Patentability for Application No. PCT/US2008/055000 dated Sep. 11, 2009.
Invitation to Pay Additional Fees for Application No. PCT/US2008/055168 dated Aug. 5, 2008.
International Search Report and Written Opinion for Application No. PCT/US2008/055168 dated Nov. 10, 2008.
International Preliminary Report on Patentability for Application No. PCT/US2008/055168 dated Sep. 11, 2009.
International Search Report and Written Opinion for Application No. PCT/US2008/055136 dated Jul. 24, 2008.
International Preliminary Report on Patentability for Application No. PCT/US2008/055136 dated Sep. 11, 2009.
Invitation to Pay Additional Fees for Application No. PCT/US2009/004866 dated Nov. 27, 2009.
International Search Report and Written Opinion for Application No. PCT/US2009/004866 dated Jan. 27, 2010.
International Preliminary Report on Patentability for Application No. PCT/US2009/004866 dated Mar. 10, 2011.
Invitation to Pay Additional Fees for Application No. PCT/US2009/004877 dated Dec. 8, 2009.
International Search Report and Written Opinion for Application No. PCT/US2009/004877 dated Feb. 12, 2010.
International Preliminary Report on Patentability for Application No. PCT/US2009/004877 dated Mar. 10, 2011.
Office Action for JP Application No. 2009-505495 filed Apr. 13, 2007, unpublished as of Aug. 3, 2012, which Office Action is dated May 8, 2012, and claims as pending for JP Application No. 2009-505495 as of May 8, 2012.
Written Opinion for Application No. PCT/US2007/009107 dated Aug. 17, 2007.
International Preliminary Report on Patentability for Application No. PCT/US2007/009107 dated Oct. 23, 2008.
Partial European Search Report for EP Application No. 11150584.8 filed Oct. 10, 2008, published as EP 2319551 on May 11, 2011, which Search Report is dated Mar. 30, 2011, and claims as pending for EP Application No. 11150584.8 as of Mar. 30, 2011.
Extended European Search Report for EP Application No. 11150584.8 dated Oct. 10, 2008, published as EP 2319551 on May 11, 2011, which Search Report is dated Jul. 26, 2011, and claims as pending for EP Application No. 11150584.8 as of Jul. 26, 2011.
International Search Report and Written Opinion for Application No. PCT/US2008/011663 dated Feb. 20, 2009.
International Preliminary Report on Patentability for Application No. PCT/US2008/011663 dated Apr. 22, 2010.
Invitation to Pay Additional Fees for Application No. PCT/US2009/000433 dated Jun. 4, 2009.
International Search Report and Written Opinion for Application No. PCT/US2009/000433 dated Sep. 25, 2009.
International Preliminary Report on Patentability for Application No. PCT/US2009/000433 dated Aug. 5, 2010.
International Search Report and Written Opinion for Application No. PCT/US2008/055021 dated Jul. 23, 2008.
International Preliminary Report on Patentability for Application No. PCT/US2008/055021 dated Sep. 11, 2009.
Response to Communication dated Jun. 6, 2012 for EP Application No. 10795810.0 filed Oct. 29, 2010, which Response is dated Dec. 14, 2012, and claims as pending for EP Application No. 10795810.0 as of Dec. 14, 2012.
International Search Report and Written Opinion for International Application No. PCT/US2010/054772 dated May 9, 2011.
International Preliminary Report on Patentability for International Application No. PCT/US2010/054772 dated May 1, 2012.
Invitation to Pay Additional Fees for PCT/US2011/043196 dated Nov. 7, 2011.
International Search Report and Written Opinion for PCT/US2011/043196 dated Feb. 17, 2012.

(56) References Cited

OTHER PUBLICATIONS

Invitation to Pay Additional Fees for PCT Application No. PCT/US2012/039369 filed May 24, 2012, which Invitation to Pay Additional Fees is dated Sep. 27, 2012, and claims as pending for PCT Application No. PCT/US2012/039369 as of Sep. 27, 2012.

Communication pursuant to Rules 161(1) and 162 EPC for EP Application No. 10795810.0 filed Oct. 29, 2010, published as EP 2493526 on Sep. 5, 2012, which Communication is dated Jun. 6, 2012, and claims as pending for EP Application No. 10795810.0 as of Jun. 6, 2012.

International Preliminary Report on Patentability for PCT/US2011/043196 dated Jan. 17, 2013.

Office Action for U.S. Appl. No. 13/178,191, filed Jul. 7, 2011, published as US 2012-0123322 on May 17, 2012, which Office Action is dated Apr. 5, 2013, and claims as pending for U.S. Appl. No. 13/178,191 as of Apr. 5, 2013.

Office Action for MX Application No. MX/A/2012/005088 filed Oct. 29, 2010, unpublished as of May 13, 2014, which Office Action is dated May 13, 2014, and claims as pending for MX Application No. MX/A/2012/005088 as of May 13, 2014.

Office Action for CN Application No. 201080060563.X filed Jun. 29, 2012, published as CN 102821798 on Dec. 12, 2012, which Office Action is dated Jul. 17, 2014, and claims as pending for CN Application No. 201080060563.X as of Jul. 17, 2014.

Office Action for EP Application No. 10795810.0 filed May 21, 2012, published as EP 2 493 526 on Sep. 5, 2012, which Office Action is dated Aug. 22, 2014, and claims as pending for EP Application No. 10795810.0 as of Aug. 22, 2014.

Office Action for JP Application No. 2012-537127 filed Apr. 27, 2012, unpublished as of Sep. 15, 2014, which Office Action is dated Aug. 19, 2014, and claims as pending for JP Application No. 2012-537127 as of Aug. 19, 2014.

Office Action for MX Application No. MX/A/2012/005088 filed Apr. 30, 2012, unpublished as of Sep. 19, 2014, which Office Action is dated Sep. 19, 2014, and claims as pending for MX Application No. MX/A/2012/005088 as of Sep. 19, 2014.

Office Action for U.S. Appl. No. 12/916,021 filed Oct. 29, 2010, published as US 2011-0105877 on May 5, 2011, which Office Action is dated Jun. 19, 2013, and claims as pending for U.S. Appl. No. 12/916,021 as of Jun. 19, 2013.

Office Action for U.S. Appl. No. 12/916,021 filed Oct. 29, 2010, published as US 2011-0105877 on May 5, 2011, which Office Action is dated Apr. 23, 2014, and claims as pending for U.S. Appl. No. 12/916,021 as of Apr. 23, 2014.

Bengtsson et al., Haemo dialysis software architecture design experiences. Proceedings of the 1999 International Conference on Software Engineering. ACM New York, NY. 1999:516-525.

Choppy et al., Architectural patterns for problem frames. IEE Proceedings: Software. Aug. 2005;152(4): 190-208.

Gentilini et al., Multitasked closed-loop control in anesthesia. IEEE Eng Med Biol Mag. Jan.-Feb. 2001;20(1):39-53.

Harel, Statecharts: A visual formalism for complex systems. Science of Computer Programming. 1987;8:231-274.

Krasner et al., A cookbook for using the model-view-controller user interface paradigm in smalltalk-80. JOOP. Aug. 1988;1(3):26-49.

Office Action for CN Application No. 201510155519.1 filed Apr. 2, 2015, published as CN 104841030A on Aug. 19, 2015, which Office Action is dated Sep. 5, 2016, and claims as pending for CN Application No. 201510155519.1 as of Sep. 5, 2016.

U.S. Appl. No. 15/960,426, filed Apr. 23, 2018, Grant et al.
U.S. Appl. No. 15/996,247, filed Jun. 1, 2018, Grant et al.
U.S. Appl. No. 16/011,294, filed Jun. 18, 2018, Van der Merwe et al.

\* cited by examiner

Section A-A

Section A-A

APPARATUS AND METHOD FOR DETECTING DISCONNECTION OF AN INTRAVASCULAR ACCESS DEVICE

CROSS REFERENCE TO RELATED APPLICATIONS

The present application is a continuation of U.S. application Ser. No. 12/916,021, filed Oct. 29, 2010, and entitled "Apparatus and Method for Detecting Disconnection of an Intravascular Access Device," which claims priority from U.S. Provisional Patent Application Ser. No. 61/256,735, filed Oct. 30, 2009 and entitled "Device and Method for Detecting Disconnection of an Intravascular Access Device," which are incorporated herein by reference in their entirety.

BACKGROUND

The present invention relates generally to systems and methods to detect disconnection of an indwelling vascular line, such as a catheter or needle, or its attached tubing. If not quickly detected, a disconnection can lead to rapid exsanguination, particularly when the blood in the catheter or tubing is under positive pressure. Examples of circumstances involving positive intravascular pressure include the positive pressure associated with an artery or arterio-venous fistula, or the positive pressure associated with an extracorporeal blood pump circuit. In hemodialysis, for example, a blood pump can generate blood flow rates of 400-500 ml/min, making rapid, reliable disconnect detection particularly desirable. Indeed any medical treatment involving relatively high flow or high pressure extracorporeal circulation (such as, for example, hemoperfusion or cardiopulmonary bypass) can be made safer by having an effective system to monitor the integrity of the arterial (withdrawal) and venous (return) blood lines.

In hemodialysis, for example, extracorporeal blood circulation can be accomplished with vascular access using either a single indwelling catheter, or two separate indwelling catheters. In a single catheter system, blood is alternately withdrawn from and returned to the body via the same cannula. A disconnection in this system can be quickly detected by placing an air monitor in the line at or near the pump inlet, because air will be drawn into the line from the disconnection site during the blood withdrawal phase of the pumping. On the other hand, in a two-catheter system, blood is typically continuously withdrawn from the body via one catheter inserted in a blood vessel or fistula, and returned to the body via the second catheter inserted in the same vessel some distance from the first catheter, or in a separate blood vessel altogether. In the two-catheter system, it is also possible to monitor for catheter or tubing dislodgement in the blood withdrawal or 'arterial' segment by using a sensor to detect the presence of air being entrained into the arterial tubing as blood is withdrawn from the blood vessel under negative pump pressure and/or positive fistula pressure. However, air-in-line detection cannot reliably detect a disconnection of the venous (return) segment of the extracorporeal circuit. In this case, if the blood-withdrawal path remains intact, air will not be introduced into the line. Thus it is particularly important to be able to detect a disruption in the continuity of the return line from the extracorporeal pump to the vascular access site.

Attempts have been made to develop systems to detect dislodgment based on the electrical, mechanical or acoustical properties of blood in the extracorporeal circuit. These systems have not been very effective because of the relatively high impedance of a blood circuit that includes long stretches of tubing, one or more blood pumps, valves, air traps and the like. Furthermore, the electrical interference generated by various devices along the blood path may obscure the signal that one is attempting to monitor.

An electrical signal can be introduced into the blood circuit through induction using a field coil surrounding a section of the blood tubing. It may also be introduced through capacitive coupling. For reasons of patient safety, the strength of an electrical signal introduced into the blood circuit necessarily must be small. However, the dielectric properties of the wall of the blood tubing can cause excessive noise or interference when attempting to detect conductivity changes in the blood from an electrical signal introduced through inductive or capacitive coupling. Therefore, it may be more desirable to introduce a brief, small electrical signal through direct contact with the blood path, to limit the length (and therefore impedance) of the blood path being monitored, and to perform the monitoring function at a suitable distance from any interference-producing components.

SUMMARY

In one aspect, the invention comprises a system for detecting whether a vascular access device, such as a needle, cannula, catheter, etc. becomes disconnected or dislodged from a blood vessel or vascular graft. The system includes a fluid delivery device that provides for the flow of a liquid through a tube or conduit into the blood vessel via an indwelling needle or catheter at a first site on the blood vessel or graft. The fluid may be an electrolyte solution or other solution suitable for intravenous infusion, or it may be blood or blood components. An electrode is disposed to be in contact or fluid communication with the lumen of the conduit, and a second electrode is disposed to be in fluid communication with blood within the blood vessel or graft via a second on the blood vessel or graft. An electronic circuit is connected to the first and second electrodes, and configured to deliver a control signal to the first and second electrodes in order to measure the electrical resistance of the fluid between the first and second electrodes, such that at least one of the electrodes is located closer to the blood vessel or graft than to the fluid delivery device. In some embodiments the electrode is located at about 50-70% of the distance from the fluid delivery device to the blood vessel or graft. In other embodiments, the electrode is located at about 70-90% or more of the distance from the fluid delivery device to the blood vessel or graft. The fluid delivery device can include a pump, either for blood or for other therapeutic or diagnostic fluid. The fluid delivery device can be part of a hemodialysis blood flow circuit, which may or may not include a blood pump, a dialyzer cartridge, or an air trap and associated tubing. The second electrode may be placed in contact with the lumen of a second conduit or tube that is in fluid communication with the blood vessel or graft at the second site. The second conduit may form part of a fluid flow path from the blood vessel or graft to the fluid delivery device. The fluid in the second conduit may be blood being delivered to an extracorporeal blood flow circuit.

The system may comprise a first and second connector connecting a pair of vascular access catheters accessing a blood vessel segment or vascular graft segment at two different sites. The first and second connectors may each connect to a flexible tube leading to the fluid delivery device. Each connector may include an electrode that is exposed to the lumen of the connector. A wire may be attached to each connector, the wire being connectable on its other end to the electronic circuit. The flexible tubes may be double lumen tubes having a first lumen for carrying fluid and a second lumen for carrying a wire. The wires of each tube may be connected on the other end of the tube to a connector for connection to the electronic circuit.

The electronic circuit or an associated microprocessor may be configured to convert the voltages measured across terminals connected to the electrodes by the electronic circuit into resistance values. The system may comprise a controller configured to receive a signal from the electronic circuit or microprocessor, the signal representing the electrical resistance between the electrodes, the controller being programmed to trigger an alert signal when the electrical resistance value exceeds a pre-determined threshold. The alert signal may be an audible or visual signal to the person whose blood vessel is being accessed, and optionally an alert signal may include an electrical command to a tubing occluder apparatus. The tubing occluder apparatus may be actuated to mechanically occlude one or more of the tubes leading from the vascular access sites. The tubing occluder may operate in a number of ways, such as, for example electromechanically, hydraulically, or pneumatically.

In another aspect, the invention comprises an apparatus for monitoring the continuity between a vascular access device and a blood vessel or vascular graft segment, comprising, a first and second vascular connector, the first connector being attached on a proximal end to a distal end of a fluid-carrying lumen of a first double-lumen tube, and the second connector being attached on a proximal end to a distal end of a fluid-carrying lumen of a second double-lumen tube. The first connector comprises a first electrode in contact with a lumen of the first connector and electrically connected to a wire within a wire-carrying lumen of the first double-lumen tube, and the second connector comprises a second electrode in contact with a lumen of the second connector and electrically connected to a wire within a wire-carrying lumen of the second double-lumen tube. The wire within the first double-lumen tube and the wire within the second double-lumen tube are each connected to an electrical connector at a proximal end of the double-lumen tubes. The distal end of each connector may be configured with a locking feature to provide a reversible, air-tight connection between the connector and a mating connector of a vascular catheter. The proximal end of the double-lumen tubes can be connected to a blood pump on an arterial side, and an air trap on a venous side; and in a hemodialysis system, the blood pump and air trap may each be reversibly connectable to a dialyzer cartridge.

In another aspect, the invention comprises a vascular connector comprising a proximal fluid connection end, a distal fluid connection end, and an electrode configured to electrically connect a fluid-carrying lumen of the connector with a wire external to the vascular connector. The proximal end of the connector may be configured to connect with a flexible tube, and the distal end of the connector may be configured to connect with a mating connector of a vascular catheter. The electrode may be installed in a conduit on the connector that connects the lumen of the connector to the exterior of the connector. The electrode may be lodged into the conduit in a manner to provide an air-tight seal between the lumen and the exterior of the connector. An elastomeric member such as an O-ring may be installed between the electrode and the conduit to contribute to the air-tight seal.

In another aspect, the invention comprises an electrical circuit for measuring the resistance of a liquid between a first and second electrode, the first electrode connected to a first terminal of the electrical circuit, and the second electrode connected to a second terminal of the electrical circuit, comprising a capacitor C1 connected on a first end to the first terminal and a capacitor C2 connected on a first end to the second terminal; a known reference resistance Rref connected on a first end to a second end of capacitor C1; switching means for connecting either (a) a first reference voltage V+ to a second end of Rref, and a lower second reference voltage V− to a second end of C2 to form a first switch configuration or; (b) the first reference voltage V+ to the second end of C2 and the lower second reference voltage V− to the second end of Rref to form a second switch configuration; and measuring means for measuring a voltage Vsense at the connection between C1 and Rref; such that the electrical circuit is configured to determine the value of the resistance of the liquid based on the known reference resistance Rref and the observed voltage Vsense for each of the first and second switch configurations. The resistance Rref may be chosen to be a value that permits conductivity measurement of an electrolyte solution or other solution suitable for intravenous infusion. The electrolyte solution may include dialysate solution. The resistance Rref may also be chosen to permit measurement of the resistance of a volume of blood between the first and second electrodes.

DETAILED DESCRIPTION

Conductivity Circuit

Figure 1:
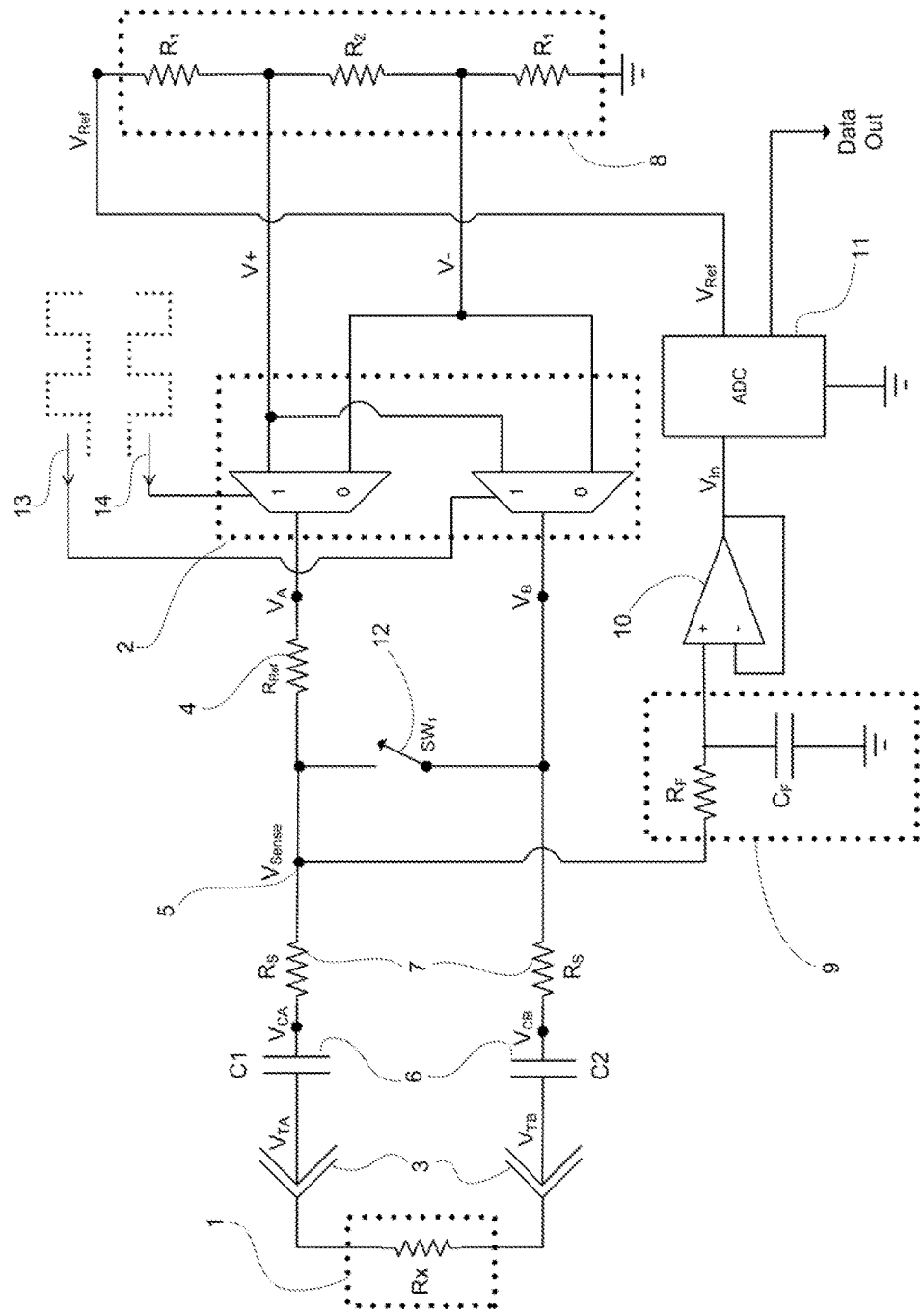
FIG. 1 is a schematic representation of a conductivity circuit in an illustrative embodiment.

An exemplary electrical circuit shown in FIG. 1 can be used to measure the electrical conductivity or resistance of a subject fluid. In one embodiment, the fluid may be an electrolyte solution or dialysate fluid, and the circuit may ultimately provide a measurement of the conductivity of the fluid to ensure its compatibility for intravascular administration. In addition to monitoring the concentration of dissolved solutes in the fluid, the electrical circuit can also monitor for any interruption in the continuity of the fluid between the electrodes connected to the circuit. For example, it can be used to monitor an intravenous fluid line for the presence of air bubbles, or for the presence of a contaminating substance. In another embodiment, the fluid may be blood, and a change in the measured electrical resistance of a blood flow path (for example, in a conduit) may be used to indicate if a discontinuity occurs between the blood flow path and measuring electrodes. For example, the blood flow path may comprise a column of blood between two electrodes that includes indwelling needles or catheters in a segment of a blood vessel, arterio-venous fistula or graft. Vascular access disconnection can result in the introduction of air into the blood flow path, causing a change in the resistivity of the blood column between the electrodes. The electrical circuit can be readily modified (depending on its application) to adjust for the difference between the impedance of a blood flow path and that of dialysate fluid.

The circuit shown in FIG. 1 may be used to measure an unknown resistance $R_x$ of a subject media 1 using inexpensive electronic components, particularly where the unknown resistance involves a conductive path through an electrolytic fluid. A switching network 2 comprising a pair of multiplexers allows the connection of nodes $V_A$ and $V_B$ to reference voltages V+ and V−. The subject media 1 having unknown resistance $R_x$ is connected to terminals $V_{TA}$ and $V_{TB}$3, and forms a voltage divider with reference resistor $R_{ref}$4. To make a conductivity measurement, alternating voltages can be presented to the subject media 1 via switching network 2 to the voltage divider created by the known reference resistor $R_{ref}$4 (680 Ω, for example, in the case of dialysate fluid) and the unknown resistance $R_X$ of the subject media 1. The midpoint of the voltage divider 5 is measured. The signal $V_{Sense}$ at point 5 is buffered by amplifier 10 to make the input signal $V_{in}$ of the analog-to-digital converter (ADC) 11. $V_{Sense}$ switches between two values as the voltage divider is driven first one way and then the other way. This signal is valid only for a short period of time after switching because the fluid in the conductivity cell 1 is AC coupled into the circuit through capacitors C1 and C2 6. Thus DC-blocking capacitors C1 and C2 6 may be used to prevent DC currents from passing through the unknown resistance (which may include a conductive path through electrolytic fluid or blood). In an embodiment, series capacitors C can each comprise two capacitors in parallel, one having a value, e.g., of 0.1 uF, and the other having a value, e.g., of 10 uF. Series resistors 7 may be used to reduce exposure by the switch network and other sense circuitry to noise and surge voltages. ADC 11 can take multiple samples of the signal as the circuit is switched between the two configurations.

Figure 2:
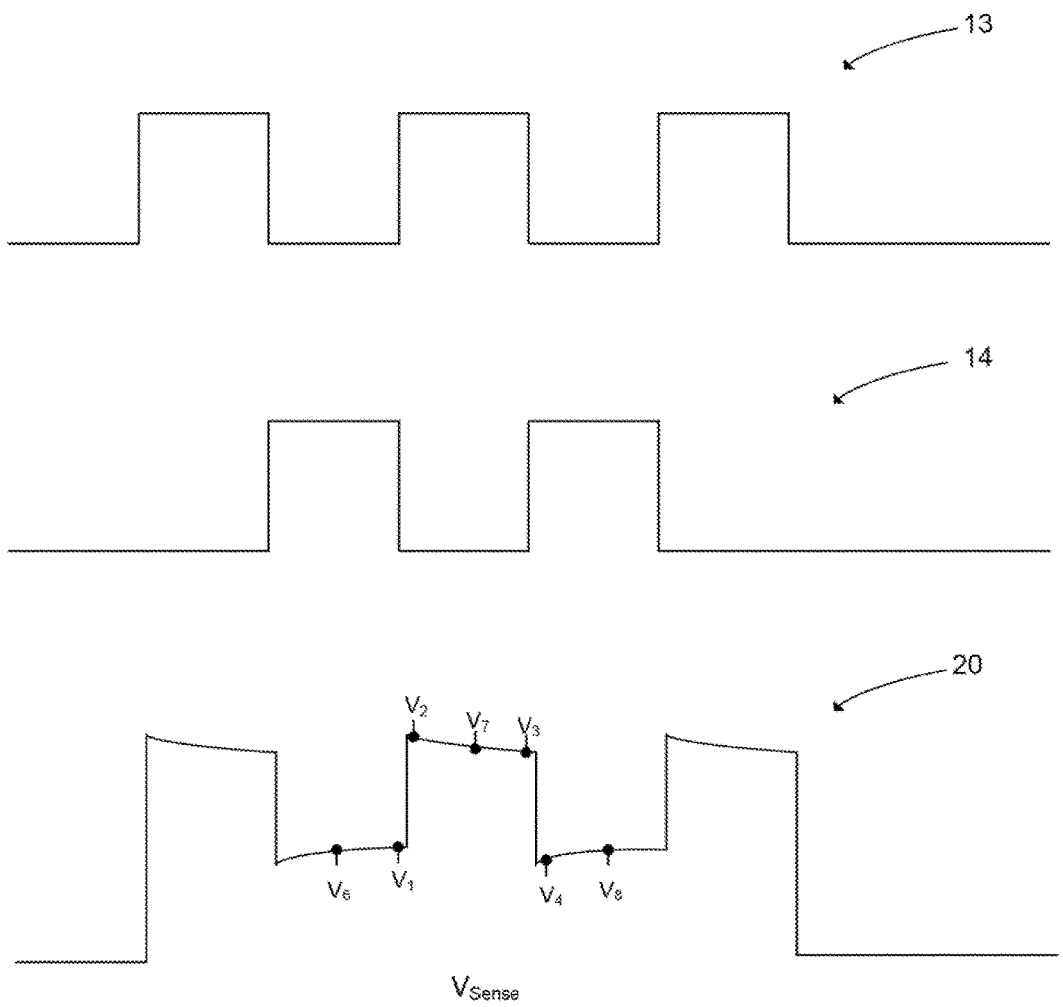
FIG. 2 is a diagram of the electrical waveforms processed by the circuit of FIG. 1.

The switching network 2 can be driven by a pair of alternating binary control signals 13, 14 that connect $V_A$ to V+ and $V_B$ to V− during one half-cycle, and $V_B$ to V+ and $V_A$ to V− during the other half-cycle. This results in a waveform at the $V_{sense}$ node 5 that is similar to the waveform 20 shown in FIG. 2. In this embodiment, $V_{ref}$ is 4 volts, resulting in a $V_{sense}$ amplitude of less than 4 volts, as shown in FIG. 2. A voltage divider 8 creates the voltages V+ and V− that are near the positive reference voltage $V_{Ref}$ and near ground, respectively. In one embodiment, R1 can have a value of 10 ohms, and R2 can have a value of 2K ohms When both multiplexers of switching network 2 are commanded to zero, the circuit is at rest and the lower voltage is presented to terminals $V_{TA}$ and $V_{TB}$ 3. When $V_A$ is high and $V_B$ is low, the higher voltage is presented to the reference resistor $R_{Ref}$ 4 and the lower voltage is presented to the subject media 1 having unknown resistance $R_x$. When $V_B$ is high and $V_A$ is low, the higher voltage is presented to the subject media 1 having unknown resistance $R_x$ and the lower voltage is presented to the reference resistor $R_{Ref}$ 4.

A change in voltage $\Delta V_{sense}$ before and after each square wave edge, can be shown to depend only on the reference resistance $R_{ref}$4, the unknown resistance $R_x$ of subject media 1, and any series resistance (including, e.g., $R_s$ 7), and is generally independent of series capacitance C1 or C2 6, since during this short time period the capacitor acts as an incremental short circuit. In particular, $$\Delta\alpha = \Delta V_{sense}/(V_+ - V_-) = (R_y - R_{ref} - R_{th})/(R_y + R_{ref} + R_{th}) = (\rho-1)/(\rho+1)$$

where $R_y = R_x + 2R_s + R_{th}$, where $R_{th}$=source series resistance from multiplexer 2 and voltage divider 8, and $\rho = R_y/(R_{ref} + R_{th})$. (Source series resistance $R_{th}$ can be derived as the sum of the resistance of multiplexer 2 and the Thevenin equivalent resistance of the voltage divider 8. For example, for R1=10 ohms, R2=2K ohms, then $R_{th}$=R1∥(R1+R2)=9.95 ohms). Thus, if $R_y$ is a short circuit, then $\rho=\infty$ and $\Delta\alpha=-1$. The sense node's change in voltage $\Delta V_{sense}$ is then equal to the voltage change at $V_B$ which has an amplitude opposite to the drive node at $V_A$. If $R_y$ is an open circuit, then $\rho=\infty$ and $\Delta\alpha=1$. The sense node's change in voltage is then equal to the voltage change at the drive node $V_A$. Accordingly, if this change in voltage is measured, the preceding equations can be solved for the unknown resistance $R_x$:

$$R_x = \rho(R_{ref} + R_{th}) - 2R_s - R_{th},$$

where $\rho=(1+\Delta\alpha)/(1-\Delta\alpha)$

As shown in FIG. 1, a low-pass filter 9 can be formed by resistor $R_f$ and capacitor $C_f$, to filter out high-frequency noise. In one exemplary arrangement, $R_F$ can have a value of 1K Ω, and $C_F$ can have a value of 0.001 uF. Buffer amplifier 10 and analog-to-digital converter (ADC) 11 can then measure the sensed voltage for a computer or digital signal processor (not shown).

The reference voltages V+ and V− may be advantageously derived from a voltage divider 8 so that V+ is close to the reference voltage $V_{Ref}$ of the ADC 11, and V− is close to the ground reference voltage of the ADC 11. For example, for $R_1$=10Ω, $R_2$=2 kΩ, and $V_{ref}$=4.0V, then V+=3.980V, and V−=0.020V. This places both voltages within but near the edges of the active sensing region of the ADC 11, where they can be used for calibration (discussed below). Switch $SW_1$ 12 may be used to help calibrate the load resistance sensing.

Several improvements may decrease errors related to variations of component values. First, a calibration step can be introduced where $V_A$ is switched to V+ for a relatively long period of time, until $V_{sense}$ settles and is approximately equal to V+, at which point ADC 11 can take a measurement of $V_{sense}$. A second calibration step can involve switching $V_A$ to V− for a relatively long period of time, until $V_{sense}$ settles and is approximately equal to V−, at which point ADC 11 can take another measurement of $V_{sense}$. This allows the ADC 11 to measure both V+ and V−.

Secondly, as shown in FIG. 2, while the square wave is switching, ADC 11 readings before and after both edges of the switching waveform may be used to compute the dimensionless quantity $\Delta\alpha$:

$$\Delta\alpha = \Delta V_{Sense}/(V+ - V-) = [(V2-V1)+(V3-V4)]/2(V+ - V-)$$

As a result, both edges of the waveform can be used to measure $\Delta V_{Sense} = [(V2-V1)+(V3-V4)]/2$, so that asymmetric responses to the circuit are likely to be canceled out. Alternatively, an average voltage at about the midpoint of the waveform may be used; so that, for example, $\Delta\alpha = \Delta V_{Sense}/(V+ - V-) = [(V7-V6)+(V7-V8)]/2(V+ - V-)$, and $\Delta V_{Sense} = [(V7-V6)+(V7-V8)]/2$. In addition, only differential measurements of the input signal $V_{in}$ of the ADC 11 can be used. Thus, any offset errors of the buffer amplifier 10 and ADC 11 can be canceled out. Also, $\Delta\alpha$ is a ratiometric quantity based on measurements using the same signal path. Thus, any gain errors of the ADC 11 can also be canceled out.

The reference resistor $R_{Ref}$ 4 may be optimally chosen to be equal to the geometric mean of the endpoints of the desired range of unknown resistances, taking series resistances $R_s$ 7 into account. For example, if $R_s = 100\Omega$ and $R_x$ varies from $100\Omega$ to $3000\Omega$, then $R_y = R_x + 2R_s$ varies from $300\Omega$ to $3200\Omega$, and $R_{ref}$ should be approximately the square root of $(300\ \Omega \cdot 3200\Omega) = 980\Omega$. To measure an unknown resistance in the range of 100 k-300 k ohms (as in, for example, a column of blood extending from one electrode to another via an arterio-venous fistula), the reference resistor $R_{ref}$ 4 can be changed to approximately 200 k ohms and the filter capacitor $R_F$ of low pass filter 9 at the input to the buffering amplifier 10 can be removed completely.

Because a voltage divider's output is a nonlinear function of its resistance ratio, errors or noise in readings from the ADC 11 produce their lowest fractional error (sensitivity) in the resultant calculation of $R_y$ when it is equal to $R_{ref}$, and the sensitivity increases the more $R_y$ diverges from the reference resistance $R_{ref}$. Specifically, it can be shown that the sensitivity in resistance ratio is as follows:

$$S_\rho = (1/\rho)\cdot\delta\rho/\delta\Delta\alpha = 2/[(1+\Delta\alpha)(1-\Delta\alpha)] = 2/[1-(\Delta\alpha)^2]$$

When $R_y = R_{ref}$, $\rho = 1$, $\Delta\alpha = 0$ and $S_\rho = 2$. Thus, for a change in $\Delta\alpha$ of 0.001 (0.1% of the ADC full-scale) around this point, the calculated resistance $R_y$ changes by 0.002 or 0.2%. The sensitivity increases as $\rho$ diverges from 1, as shown in Table 1.

TABLE 1

| $\rho$ | $\Delta\alpha$ | $S_\rho$ |
|---|---|---|
| 1 | 0 | 2 |
| 2, 0.5 | ±0.333 | 2.25 |
| 4, 0.25 | ±0.6 | 3.13 |
| 5.83, 0.172 | ±0.707 | 4 |
| 10, 0.1 | ±0.818 | 6.05 |
| 20, 0.05 | ±0.905 | 11.03 |

Figure 3:
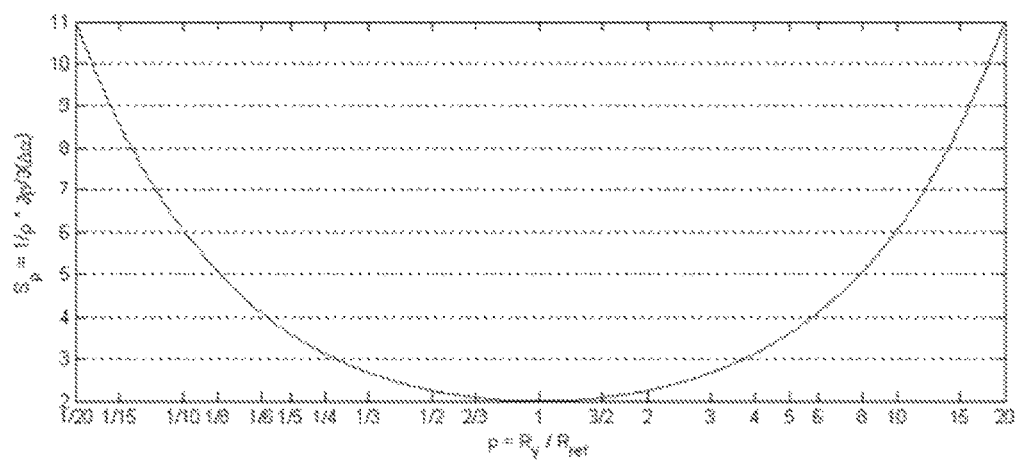
FIG. 3 is a representative graph of the noise/error sensitivity of the circuit of FIG. 1 plotted against the ratio of unknown/reference resistance in the circuit.

FIG. 3 shows that the noise/error sensitivity doubles at about a 6:1 ratio of unknown/reference resistance, and triples at a 10:1 ratio. Resistance measurements outside this range may suffer in their increased sensitivity to noise and error.

For calibration purposes, a switch $SW_1$ 12 can be used to make resistance measurements to calibrate out a point at $R_x = 0$. Preferably this switch 12 should be placed across the terminals $V_{TA}$ and $V_{TB}$ 3, or as close to the terminals as feasible, which would give a true zero-point calibration. In practice, however, locating the switch 12 close to the terminals $V_{TA}$ and $V_{TB}$ 3 may make the switch 12 prone to external noise and surge voltages, and may introduce DC leakage current into the subject media 1.

The series capacitances C1 and C2 6, and the use of square waves are important for unknown resistances that include an electrolytic conductive path. There are at least two reasons for this. First, it may be important in many applications to prevent DC current from flowing through an electrolyte solution or a bodily fluid having similar properties; otherwise electroplating and/or electrolysis of electrodes at the terminals $V_{TA}$ and $V_{TB}$ 3 can occur. In this circuit, the capacitors C1 and C2 6 block DC currents. Furthermore, because the capacitors may allow very small currents to flow (microamps or less), using an alternating square wave voltage may help to limit the average current further.

Secondly, in the event that a small electrochemical DC voltage is induced in the subject media 1 (for example, the electrodes in a fluid path may oxidize over time at different rates), this DC voltage can be blocked by the capacitors C1 and C2 6. Because the method for calculating resistance takes differential measurements, any residual DC voltage may be canceled out through the process of calculating the unknown resistance Rx of subject media 1.

Vascular Disconnect Detector

With the appropriate modifications of a conductivity measurement circuit such as the one described above, it is possible to detect the conductivity and changes in the conductivity of blood. More specifically, it is possible to detect the change that occurs in the conductivity of a volume of blood when air enters the volume. This situation can occur, for example, when an intravascular access site becomes dislodged in an extracorporeal blood circuit.

The circuit shown in FIG. 1 can be used to measure the resistance of a volume of fluid in a conductivity cell or conduit 1. For measurements of $R_x$ of a conductivity cell 1 representing the resistance or conductivity of a volume of dialysate solution, a convenient value for the reference resistor $R_{Ref}$ 4 can be chosen to be approximately 680 ohms. For measurements of $R_x$ of a conduit 1 representing the resistance or conductivity of a column of blood extending from a first cannula or needle, through an arterio-venous fistula, to a second cannula or needle, a convenient value for the reference resistor $R_{Ref}$ 4 can be chosen to be approximately 200 k ohms.

The advantages of using this circuit to monitor the continuity of a column of a bodily fluid such as blood or plasma include the following:

Capacitive coupling to the conductivity cell or conduit 1 blocks DC current which could cause plating and corrosion of electrodes at terminals VTA and VTB;

Voltages and current levels are very low and decoupled for patient safety;

Current only flows briefly while the measurement is being taken. No current flows between measurements.

With the lower reference resistor $R_{ref}$ 4 value (e.g. 680 ohms), this circuit is appropriately configured for dialysate conductivity measurements. With a much higher reference resistor $R_{ref}$ 4 value (e.g. 200 k ohms) this circuit is appropriately configured for measuring the resistance between an arterial needle and a venous needle to detect vascular needle dislodgement from an arterio-venous fistula.

Electrode Placement

The continuity of a fluid column leading from a fluid delivery apparatus to a patient's blood vessel or vascular graft can be monitored using the electronic circuit described above. The fluid being delivered may include blood or any electrolyte solution, including dialysate fluid. Although the following discussion will involve a hemodialysis system, the same principles of operation of the invention can apply to any device that is configured to deliver a fluid to a patient via a vascular access. In an embodiment illustrated by FIG. 4, the conductivity of a volume of blood or other fluid within a fluid flow circuit 100 of a hemodialysis machine 200 can be monitored electronically, using electrodes on each end of the volume that make direct contact with the blood or other fluid. Using an electrical circuit such as the one shown in FIG. 1, one electrode can be connected to the $V_{TA}$ terminal, and the other electrode can be connected to the $V_{TB}$ terminal of the circuit. The voltages applied to the electrodes by the circuit can be sufficiently small (e.g., about 4 volts or less), sufficiently brief, and with DC voltages sufficiently decoupled so as to prevent any harm to the patient. In this example, a fluid flow circuit 100 is shown, including an arterial access needle 102, an arterial catheter tubing 104, an arterial catheter tubing connector 106, arterial blood circuit tubing 108, a transition 110 between the blood circuit tubing 108 and hemodialysis machine 200, a blood pump inlet line 112, a blood pump 114, a blood pump outlet line 116, a dialyzer 118, a dialyzer outlet line 120, air trap 122, a transition 124 between hemodialysis machine 200 and venous blood circuit tubing 126, a venous catheter tubing connector 128, a venous catheter tubing 130, a venous access needle 132, and the intraluminal volume of that portion of the patient's blood vessel or fistula 134 that lies between the arterial access needle 102, and the venous access needle 132. It should be noted that the invention described herein also encompasses circumstances in which the arterial access needle may reside in one blood vessel of a patient, while the venous access needle may reside in a separate blood vessel some distance away from the arterial access site. Furthermore, the circuit described above may be used to monitor the integrity of a vascular access in a fluid delivery system that does not have the venous return line shown in FIG. 4. In that case, for example, an electrode at location B could be paired with an electrode in contact with fluid in a dead-end line communicating with a second needle or cannula accessing the blood vessel or vascular graft. In another example, an indwelling hollow cannula or solid trocar in the vascular segment can be equipped with a conductive wire which could then serve as the second electrode in the monitoring system. The vascular segment being accessed may be a surgically constructed arterio-venous fistula, and may also include an artificial conduit such as a Gortex vascular graft. The term 'arterial' is used herein to denote the portion of the blood flow circuit that conducts blood away from the patient and toward the hemodialysis machine 200. The term 'venous' is used to denote the portion of the blood flow circuit that conducts blood away from the hemodialysis machine 200 and back toward the patient. The term 'access needle' is used to denote a needle or catheter device that penetrates the patient's vascular segment or fistula. In different embodiments it may be permanently fused or reversibly connected to a corresponding catheter tubing 104, 130.

The continuity of any segment of the fluid flow circuit 100 can be monitored by positioning two electrodes in contact with the fluid on either side of the fluid and blood-containing segment of interest. In order to monitor for a disconnection of the arterial access needle 102, or the arterial catheter tubing 104, or the venous access needle 132 or venous catheter tubing 130, one electrode can be placed in continuity with the lumen of the venous side of the blood flow circuit, while a second electrode is placed in continuity with the lumen of the arterial side of the blood flow circuit. In one embodiment, the two electrodes can be positioned on or near the dialysis machine 200, with an electrode in contact with blood upstream of blood pump 110, and a second electrode in contact with blood downstream of the dialyzer 118 and/or air trap 122. For example, the electrodes can be incorporated into transition locations 110 and 124.

In another embodiment, one of the electrodes can be positioned to be in contact with the fluid in the fluid flow circuit 100 at a point that is closer to the vascular access site 134 than it is to the equipment (e.g. a dialysis machine) used to deliver fluid flow to the accessed blood vessel or vascular graft. In a preferred embodiment, both electrodes can be positioned to be nearer to the patient's blood vessel or vascular graft than the equipment associated with the dialysis machine 200. This may further reduce electrical interference associated with the dialysis machine 200. An electrode A can be conveniently placed at or near the arterial catheter tubing connector 106 and a second electrode B can be conveniently placed at or near the venous catheter tubing connector 128. In this arrangement, the electrical continuity pathway from the first electrode through the patient's vascular access to the second electrode is much shorter—and the electrical resistance lower—than the pathway extending back toward the dialysis machine 200. In some cases, the access catheters 104 and 130 can be as short as about a foot, whereas the arterial and venous tubings 108 and 126 can be about six feet long. Because of the electrical conductive properties of the fluid in the circuit, the electrical resistance associated with the pathway incorporating tubing 108 and 126, and components of the dialysis machine 200, can be many times greater than the electrical resistance associated with the pathway through the patient's blood vessel or fistula 134.

Electrical interference associated with the dialysis machine 200 is thus reduced, and a change in electrical resistance due to an access-related disconnection can more easily be detected. Preferably, the electrodes A and B are positioned to be more than 50% of the distance from the dialysis machine to the patient. More preferably (and more conveniently), the electrodes A and B are located near the last disengageable fluid connection before reaching the patient. In one embodiment of a hemodialysis system, the blood tubing 108 and 126 is approximately 6 feet in length, and the arterial and venous catheter tubes 104, 130 are about two feet or less in length. A convenient location for electrodes A and B would then be at the arterial line and venous line connectors 106, 128 (which can be, e.g. Luer type connectors or modifications thereof) that connect the arterial and venous blood circuit tubes 108, 126 with the arterial and venous catheter tubes 104, 130.

Connector Electrodes

Figure 5A:
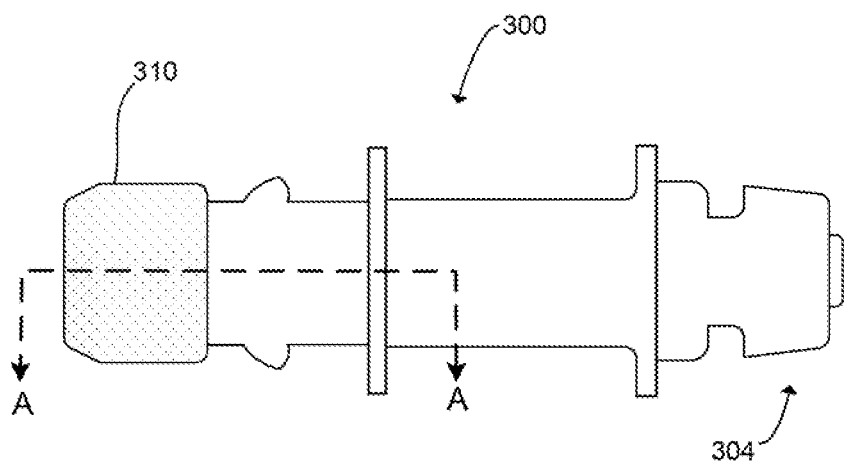
FIG. 5A is a side view of a connector that may be used in the blood flow circuit of FIG. 4.
Figure 5B:
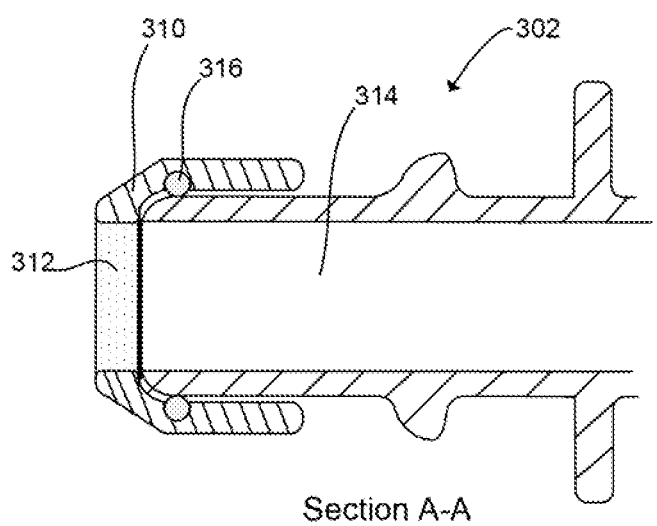
FIG. 5B is a cross-sectional view of the connector of FIG. 5A.

As shown in FIGS. 5A and 5B, in one embodiment, a blood line connector for the blood circuit of a hemodialysis system may incorporate electrodes that can make contact with any liquid within the lumen of the connector. In one aspect, the electrode can comprise an annular conductive cap 310 placed at the tube-connection or proximal end 302 of any suitable connector, such as, for example connector 300. The electrode is preferably constructed from a durable and non-corrosive material, such as, for example, stainless steel. The distal coupling end 304 of connector 300 can be constructed to make a sealing engagement with a corresponding Luer-type connector of an arterial or venous catheter, for example. The inner annular surface 312 of the cap 310—in part or in whole—can make contact with any liquid present within the lumen 314 of the connector. As shown in FIG. 5B, an O-ring 316 or a suitable sealant can be placed between the cap electrode 310 and the proximal end 302 of the connector to maintain a fluid-tight connection between the connector and any flexible tubing attached to the connector.

An elastomeric O-ring may be particularly useful in hemodialysis or other extracorporeal systems in which the blood-carrying components are subjected to disinfection or sterilization using heated liquids. The thermal coefficients of expansion of the plastic components of a connector may be sufficiently different from that of an incorporated metal electrode that a permanent seal may not be preserved after one or more sterilization or disinfection procedures. Adding an elastomeric component such as an O-ring at the junction between an electrode and the connector seat on which it is positioned may preserve the seal by accommodating the different rates of expansion and contraction between the electrode and the connector.

Figure 6:
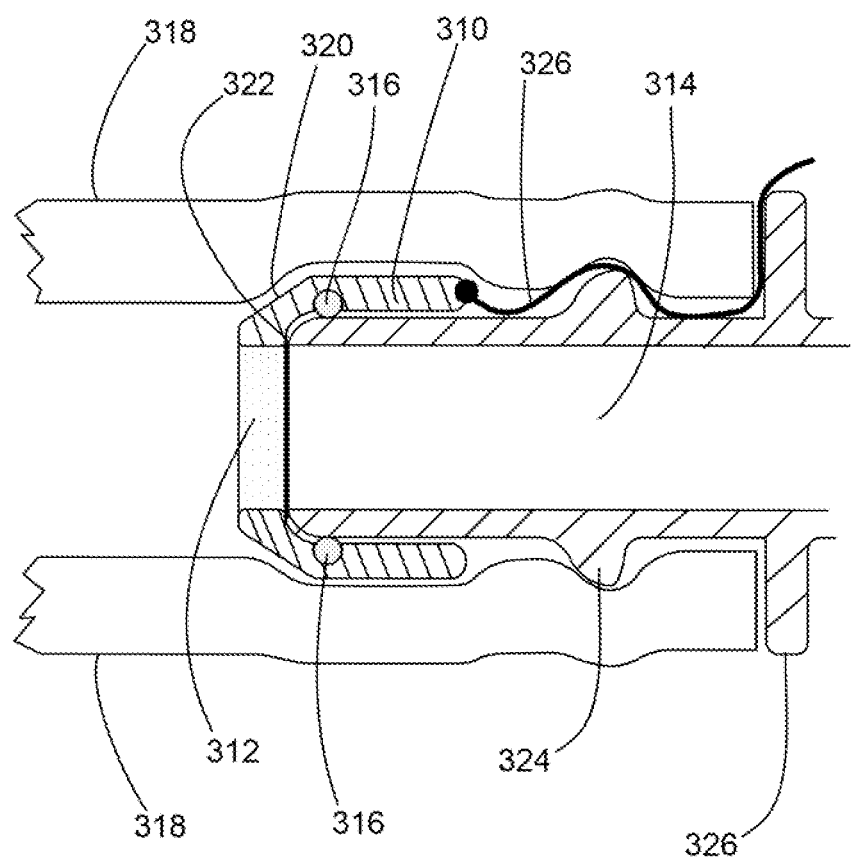
FIG. 6 is a cross-sectional view of the connector of FIGS. 5A and 5B, with an attached wire and flexible tubing.

As shown in FIG. 6, in one embodiment, a conductive electrode 310 (constructed of, e.g., stainless steel) can be incorporated into a portion of a connector 300 (either at its proximal end 302, or alternatively at its distal connecting end 304), over which the end of a flexible tubing 318 can be placed. In this embodiment, the electrode 310 is generally cylindrical, and has a taper 320 on a proximal end to permit an easier slip-fit attachment of the end of a segment of flexible tubing 318 over the outside surface of the electrode 310. As shown in FIG. 6, the internal surface of the electrode 310 has an internal ledge 322 that allows the electrode cap 310 to slip over and abut a proximal end 302 of connector 300. Connector 300 can be constructed of any suitable hard material, including metal or more typically a plastic material. The ledge 322 helps to ensure that a smaller diameter inner surface 312 of electrode 310 is properly positioned to make contact with any liquid (e.g. blood) that passes through the lumen 314 of connector 300. The connections between connector 300 and electrode 310, and electrode 310 and the termination of an overlying flexible tubing 318 can be made air tight or permanent with any suitable adhesive compatible with the compositions of the components.

To ensure a more secure seal to prevent blood leakage between the connector and electrode, and to limit the area under the electrode where blood elements may migrate and become lodged, an O-ring 316 can be incorporated into the inner surface of electrode 310 near the electrode internal ledge 320. This is seen in enlarged detail in FIG. 6. In this example, the O-ring 316 seals between the stainless steel electrode 310 and the distal end 302 of connector 300. A barb element 324 on the proximal end 302 of connector 300 can be incorporated in the connector design in order to hold the stretched end of the flexible tubing 318 onto the proximal end 302 of connector 300. In an embodiment, the electrode 310 is held in place by the portion of the flexible tube that is stretched over both the electrode 310 and the barb 324 of connector 300.

A wire 326 can be soldered, welded or otherwise secured onto the outer surface of electrode 310, and can travel under the overlying stretched tubing 318 until exiting more distally along the connector 300. The wire can thus conduct electrical signals to and from the electrode 310 as the internal surface 312 makes contact with the intraluminal fluid (e.g. blood). In the example shown, wire 326 is soldered to a distal portion of electrode 310 and travels under tubing 318, to emerge at the abutment of tubing 318 with a corresponding stop 326 of connector 300.

Figure 7A:
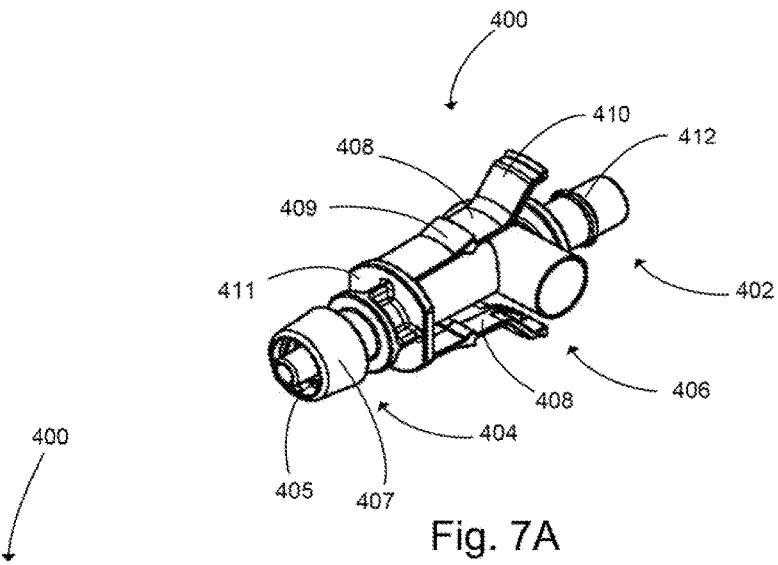
FIG. 7A is a perspective view of an alternate embodiment of a connector that may be used in the blood flow circuit of FIG. 4.
Figure 7B:
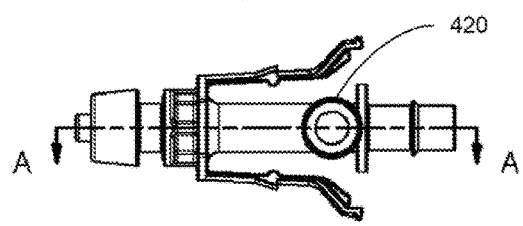
FIG. 7B is a top view of the connector of FIG. 7A.
Figure 7C:
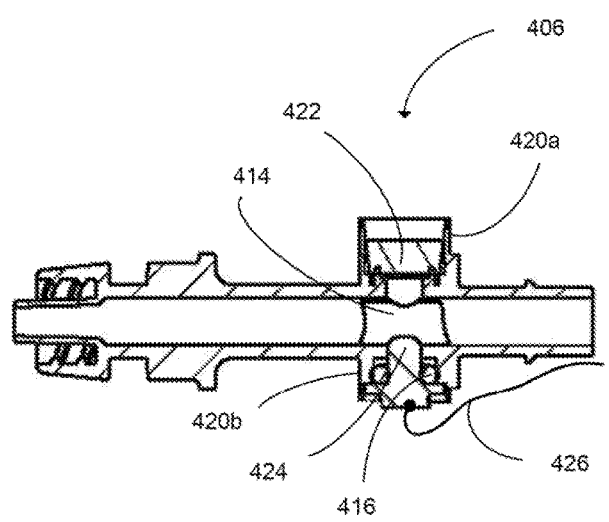
FIG. 7C is a cross-sectional view of the connector of FIG. 7B.

In another embodiment as shown in FIGS. 7A-7C, a connector 400 as described in U.S. Patent Application Publication No. 2010/0056975 (the contents of which are hereby incorporated by reference) has been modified so that a mid-portion 406 of the connector 400 can incorporate an electrode. Placement of the electrode along the mid-portion 406 of the connector 400 avoids having to alter the distal coupling end 404 of the connector, and avoids any alteration of the interaction between the termination of the flexible tubing and the proximal end 402 of the connector. In this example, the blood line connector 400 is constructed to make two different types of sealing connections on its distal coupling end 404, including an internal screw-type connection 405 for a Luer-type connector of a patient access line, and an external press-in type connection 407 with a dialysis machine port for recirculation of priming and disinfecting fluid through the blood carrying components of a dialysis system. The press-in feature 407 is formed having a frustoconical shape on the outside surface of the distal end 404 of the connector 400, while the Luer-compatible screw-type feature 405 is formed on the corresponding internal surface of the distal end 404 of the connector 400. The outside surface of the frustoconical member is constructed to make sealing engagement with the seat of a mating connector of a dialysis machine 200 or other device. A pair of locking arms 408 extending proximally from the distal coupling end 404 of the connector 400 can each have a barbed portion 409 to engage a corresponding locking feature on a mating connector on the dialysis machine, and a finger depression portion 410 to aid in disengaging the barbed portions 409 from the dialysis machine. The barbed portion 409 helps to lock the frustoconical member in sealing engagement with its mating connector on the dialysis machine when making a press-in type of connection. The distal ends of the locking arms can be constructed to attach to the connector via a flange 411 located proximal to the frustoconical portion 407 of the connector 400. The connector 400 has a proximal tubing attachment end 402 to sealingly engage a flexible tube. The tubing attachment end 402 may have one or more barb features 412 to help prevent disengagement of the end of a flexible tube from the connector 400.

FIG. 7B shows a side view of connector 400, bringing into view an access feature or port 420 that can permit placement of an electrode in direct communication with the lumen of connector 400. In other embodiments, the access feature may house an elastomeric stopper—with or without a septum—to permit sampling of fluid from within the lumen 414 of connector 400 using a syringe with a sharp or blunt needle. Alternatively, the feature may serve as a port to allow connection of another fluid line to the lumen 414 of connector 400.

In yet another embodiment, the mid-portion 406 of connector 400 may have two access ports, as shown in the cross-sectional view of FIG. 7C. A fluid access port 420a can serve as a sampling port, and an electrode port 420b can serve as an electrode cradle. An elastomeric stopper 422 within sampling port 420a can be shaped to extend to the lumen 414 of connector 400, simultaneously permitting sampling of fluid in the lumen 414 with a needle, while maintaining an air-tight seal. Alternatively, a Luer-type connector having a septated cap or seal can be incorporated into the port, which is capable of connecting with a syringe or catheter having a mating Luer-type connector. An electrode port 420b can serve as a seat or cradle for an electrode 424. In can be press-fit or cemented into position, and sealed with an adhesive, or with an O-ring 416 as shown. A wire 426 can be soldered, welded or otherwise secured onto the outer surface of electrode 424, and can travel proximally toward dialysis machine 200 with the arterial tubing 108 or venous tubing 126 to which connector 400 is attached.

In any of the above electrode embodiments, the electrodes may be replaced by a suitably sized thermistor, or combination of a thermistor and electrical conductor, for the additional purpose of monitoring the temperature of the fluid passing through connector 300, 400 or variants thereof.

Wire Assembly

In one embodiment, the wires carrying electrical signals to or from a pair of electrodes on connectors 106, 128 (one on the arterial side and one on the venous side of the blood flow circuit) can travel separate and apart from the blood tubing 108, 126 back toward dialysis machine 200, where they ultimately terminate and connect to, a conductivity detecting circuit, such as the conductivity circuit shown in FIG. 1. The conductivity circuit, in turn, provides an appropriately configured signal to a processor on the dialysis machine to determine whether a change in fluid conductivity consistent with an access disconnection has occurred. If so, the processor can trigger an alarm condition, or can initiate a shut-down of blood pump 114, and trigger a mechanical occlusion of blood tubing 108 and/or 126, for example.

Figure 8A:
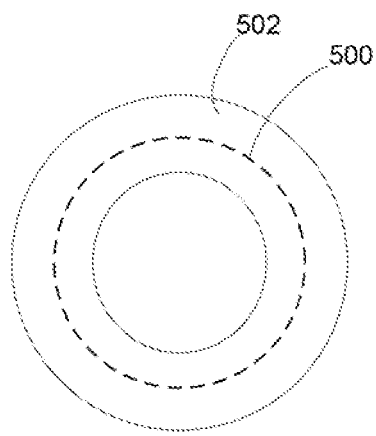
FIGS. 8A-D are various cross-sectional views of a flexible tube incorporating a conductive wire.
Figure 8B:
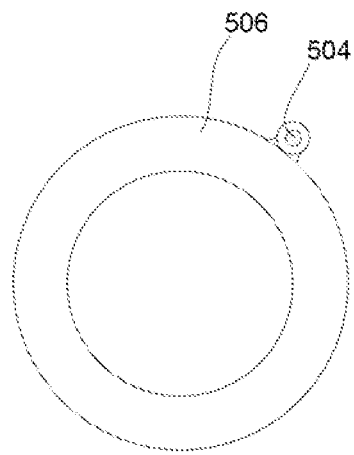
Figure 8C:
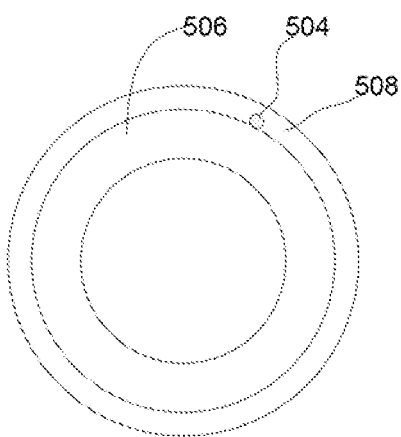
Figure 8D:
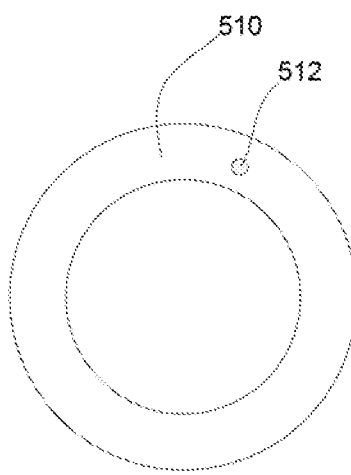

Wires that extend together or separately between the dialysis machine and the patient are at risk of getting tangled, broken or becoming disconnected. Therefore, preferably, each wire 326 or 426 can be attached, fused, or otherwise incorporated into its associated tubing 108, 128. Incorporating a wire into its associated tubing provides a convenient way of protecting the wires and connections, and simplifying the interface between the patient and the dialysis apparatus. Exemplary methods of achieving this are shown in FIGS. 8A-8D. In a preferred embodiment, the tubing is comprised of a flexible material (e.g., silicone) that can be formed in an extrusion process. As shown in FIG. 8A, a loose wire mesh may be embedded in the flexible silicone tubing as it is formed and extruded, similar to fiber reinforcement of flexible tubing. As shown in FIG. 5A, a wire mesh 500 can be embedded within the wall of the flexible tubing 502 during extrusion, in a manner similar to the construction of a fiber-reinforced tube. As shown in FIG. 8B, an insulated wire 504 can be joined to the external surface of its adjacent tubing 506, either during a secondary extrusion process, or a process in which the two structures are joined by an adhesive, for example. As shown in FIG. 8C, a second extrusion producing a secondary concentric layer of tubing material 508 can be made to capture a wire running along the external surface of the tubing after the primary extrusion. As shown in FIG. 8D, the tubing 510 during formation can also be co-extruded with a wire 512 embedded in the wall of the tubing.

Figure 9:
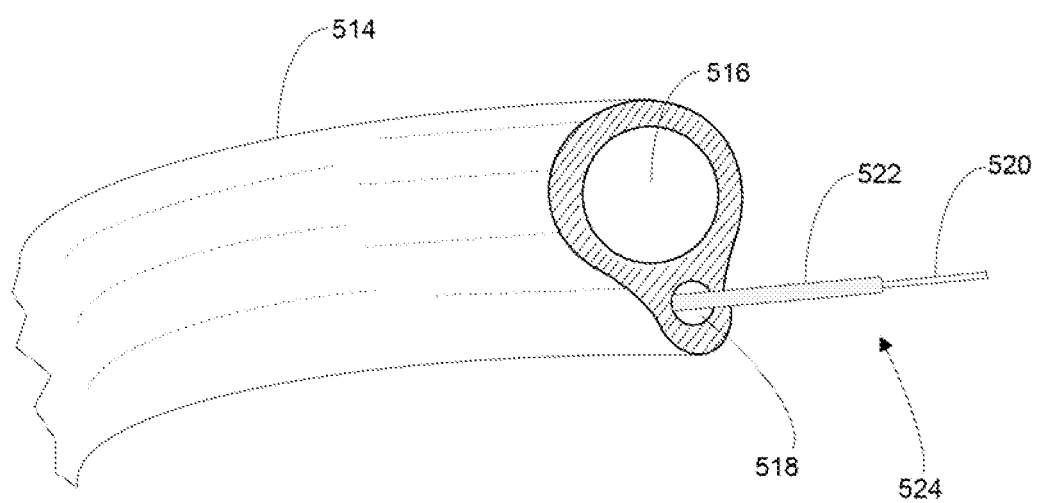
FIG. 9 is a perspective view of a flexible double-lumen tube having a fluid-carrying lumen and a wire-carrying lumen.

In some of the above methods, the resulting tube-wire combination may have a tendency to curl because of the difference in thermal coefficients of expansion between the wire and the silicone material of the tubing. As the material cools after extrusion, the silicone may capture the embedded wire tightly, causing the cooled tube-wire bundle to curl. In a preferred embodiment, the wire lumen of the extrusion die is constructed to be large enough to accommodate a cross-sectional area significantly larger than the cross-sectional area of the wire to be embedded. Then as the silicone cools, the passageway surrounding the wire does not shrink to the point of tightly encasing the wire. A co-extrusion process incorporating an insulated wire can generate a tube-wire bundle as shown in FIG. 9. In this example, flexible tubing 514 is a co-extrusion of a fluid-carrying lumen 516 and a wire-carrying lumen 518. Preferably, the wire 520 is multi-stranded for flexibility and durability, and is coated or sheathed in a durable, flexible synthetic insulating material 522, such as, for example, PTFE. A PTFE-based sheath 522 of the stranded wire 520 can sustain the high temperatures associated with the silicone tubing extrusion process, so that its integrity is maintained along the section 524 of the wire that ultimately exits the tubing for connection either to the dialysis machine 200 or the patient line connectors 106, 128. A coating or sheathing may also help prevent the wire from adhering to the side walls of the wire-carrying lumen after extrusion and during cooling.

Figure 10:
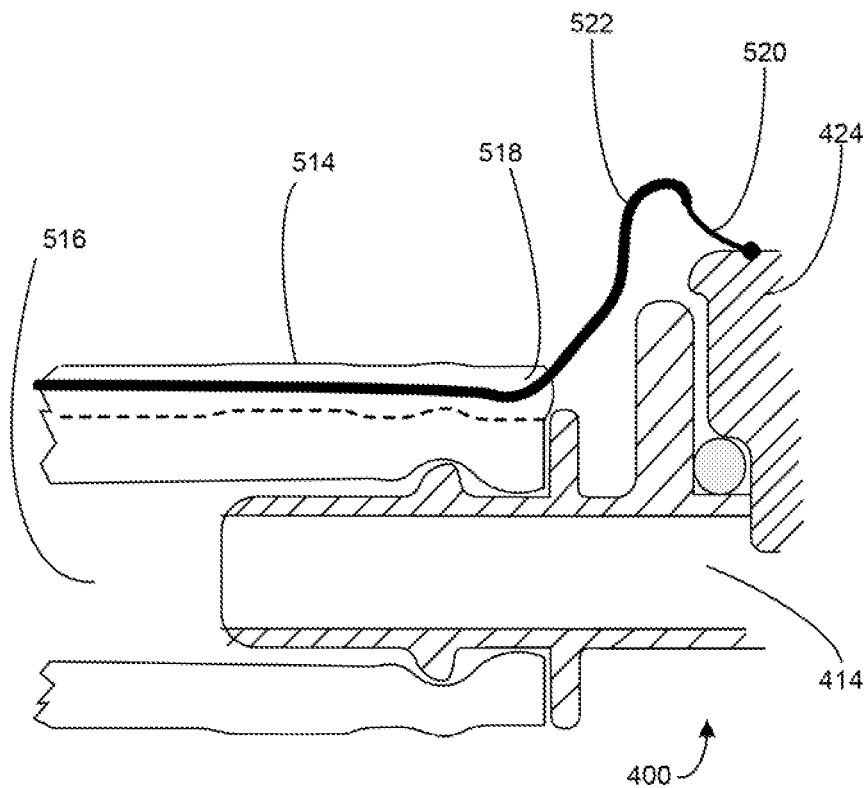
FIG. 10 is a cross-sectional view of a connector similar to the connector of FIGS. 7A-C, with an attached wire and tubing.

FIG. 10 shows a cross-sectional view of an exemplary connector-wire-tubing assembly. The proximal tubing connection end of a connector 400 is shown with the end of a double-lumen tubing 514 attached. The fluid-carrying lumen 516 is press-fit and/or cemented to the proximal end of connector 400, allowing for fluid flow through the central lumen 414 of connector 400. Stranded wire 520 is soldered or otherwise attached to electrode 424, which is in conductive contact with any fluid present within the lumen 414 of connector 400. The non-connecting portion of the wire 520 that travels outside tubing 514 is preferably sheathed in an insulating synthetic coating, such as, for example, PTFE. Optionally, this portion of both the exposed and sheathed wire may also be sealed with a sealant, such as RTV. The sheathed wire 522 enters the wire-carrying lumen 518 of tubing 514 near its termination onto connector 400. The wire/tubing bundle then makes its way toward the dialysis machine 200, where the wire emerges from the tubing to make a connection to a conductivity circuit such as the one shown in FIG. 1.

Figure 11:
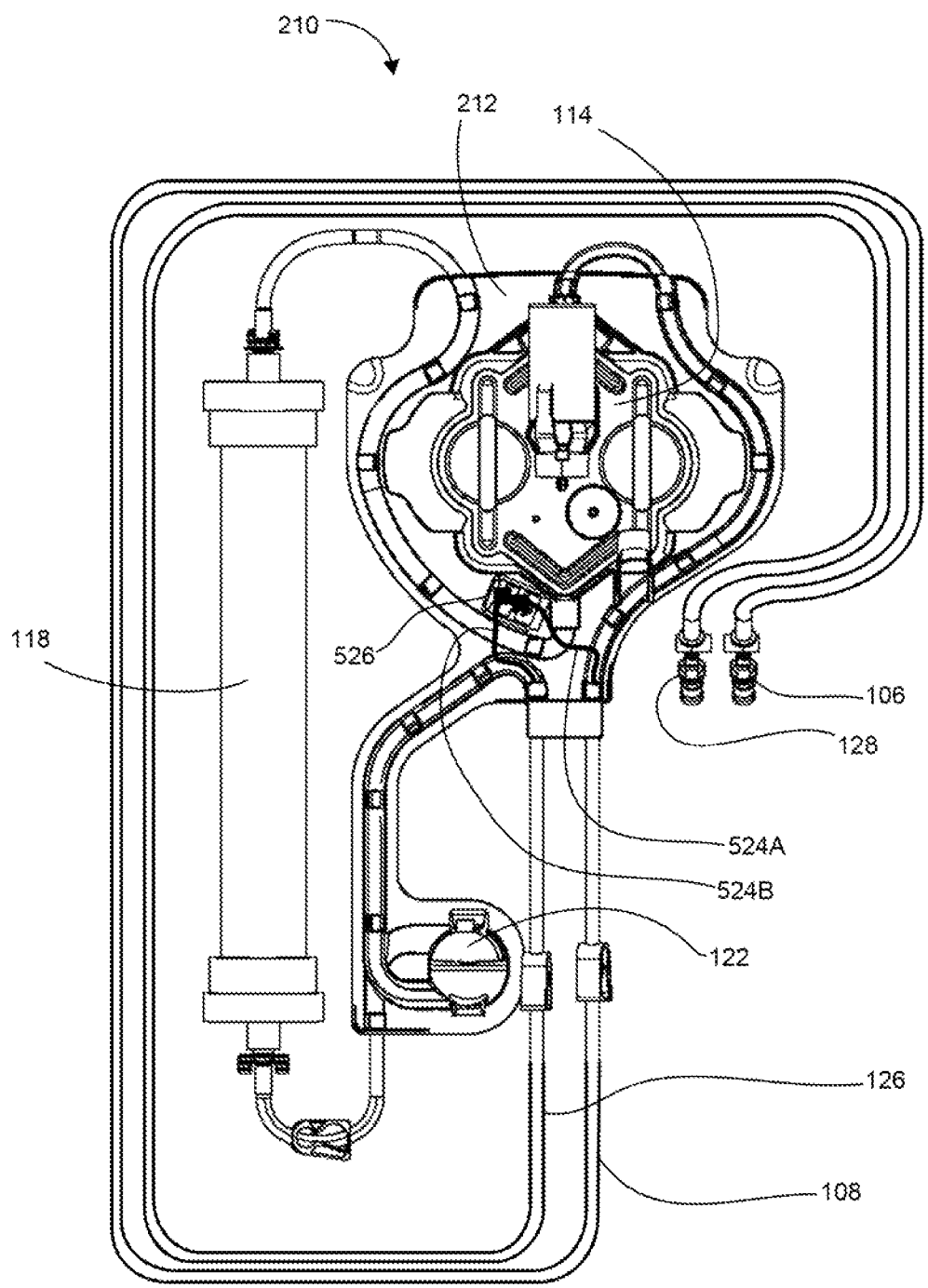
FIG. 11 is a plan view of an extracorporeal blood flow circuit used in a representative hemodialysis system.
Figure 12:
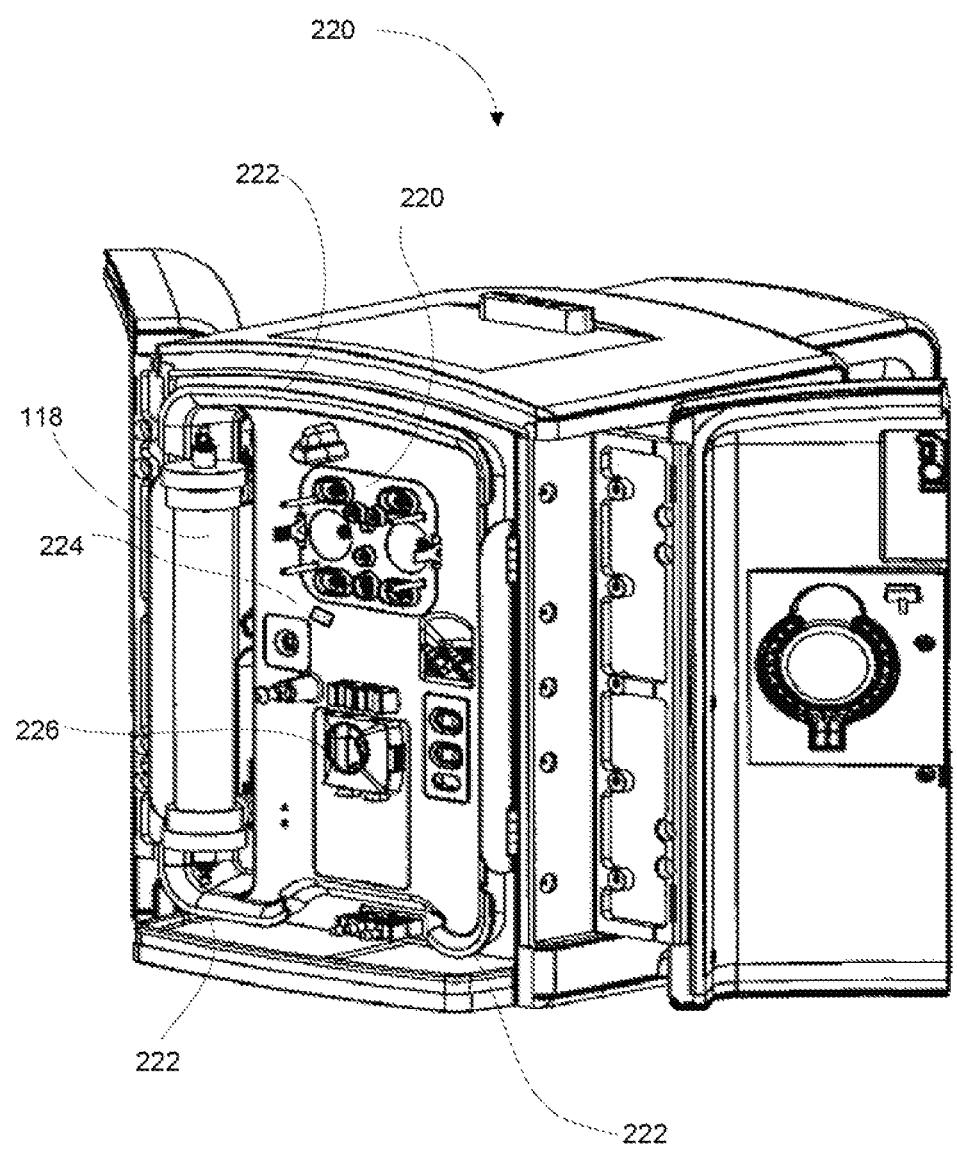
FIG. 12 is a perspective view of a hemodialysis apparatus configured to receive and operate the extracorporeal blood flow circuit of FIG. 11.

FIG. 11 shows an exemplary extracorporeal circuit 210 that may be used as a removable, replaceable unit in a hemodialysis apparatus 220 as shown in FIG. 12. In this embodiment, the extracorporeal circuit comprises a blood pump cassette 114, dialyzer 118, venous return air trap 122, arterial blood tubing 108, venous blood tubing 126, arterial catheter connector 106, and venous catheter connector 128. The arterial 106 and venous 128 connectors may be of a type similar to the connector 300 shown in FIGS. 5A and 5B, or similar to the connector 400 shown in FIGS. 7A-7C, or variants thereof. The arterial 108 and venous 126 blood tubes may be of a type shown in FIGS. 8A-8D, or FIG. 9. Wires forming terminal connections to electrodes on connectors 106 and 128 may exit arterial 106 and venous 126 tubes as segments 524A and 524B to make a connection with a connector that ultimately passes the connection through on the dialysis apparatus to terminals associated with a conductivity circuit such as that shown in FIG. 11n the embodiment shown, the connector 526 is mounted to a support structure 212 for the blood pump 114 and air trap 122.

FIG. 12 shows an exemplary hemodialysis apparatus 220 that is configured to receive the extracorporeal circuit 210 shown in FIG. 11. In this illustration, the dialyzer 118 is already mounted onto the apparatus 220. A base unit 220 receives the control ports of a mating blood pump cassette 114. Sets of raceways or tracks 222 help to organize the pair of arterial 106 and venous 126 blood tubes when not extended out and connected with a patient. A connector 224 receives and passes through the connections made between wire segments 524A and 524B and connector 526 to the terminal connections of a conductivity circuit such as that shown in FIG. 1. A tubing occluder 226 is positioned to receive venous blood tube 126 after it exits air trap 122, and arterial blood tube 108 before it reaches blood pump cassette 114. The occluder 226 may be actuated pneumatically or electromechanically, for example, whenever an alarm condition occurs that requires cessation of extracorporeal blood flow. A set of arms of occluder 226 can be configured to rotate against the walls of the flexible tubes, constricting or stopping fluid flow within them. Thus, a controller installed within apparatus 220 can receive a signal from a conductivity circuit similar to FIG. 1, the signal representing the electrical resistance of the column of fluid or blood between the electrodes mounted on connectors 106 and 128. Because the connectors are positioned much closer fluidically to the patient's blood vessel or fistula 134 than to the blood pump 114, dialyzer 118 and air trap 122, the signal associated with the fluid path through the blood vessel or fistula 134 can discriminate between an intact and an interrupted column of blood or fluid between the connectors 106/128 and the patient's blood vessel or fistula 134. The controller can be programmed to respond to an electrical resistance detected by the conductivity circuit found to exceed a pre-determined value. Depending on the circumstances, the controller may then trigger an alarm to alert the patient to a possible disconnection of blood flow, and may also optionally command the occluder 226 to cease extracorporeal flow to and from the patient.

Operation of the Disconnect Detection Circuit

Figure 4:
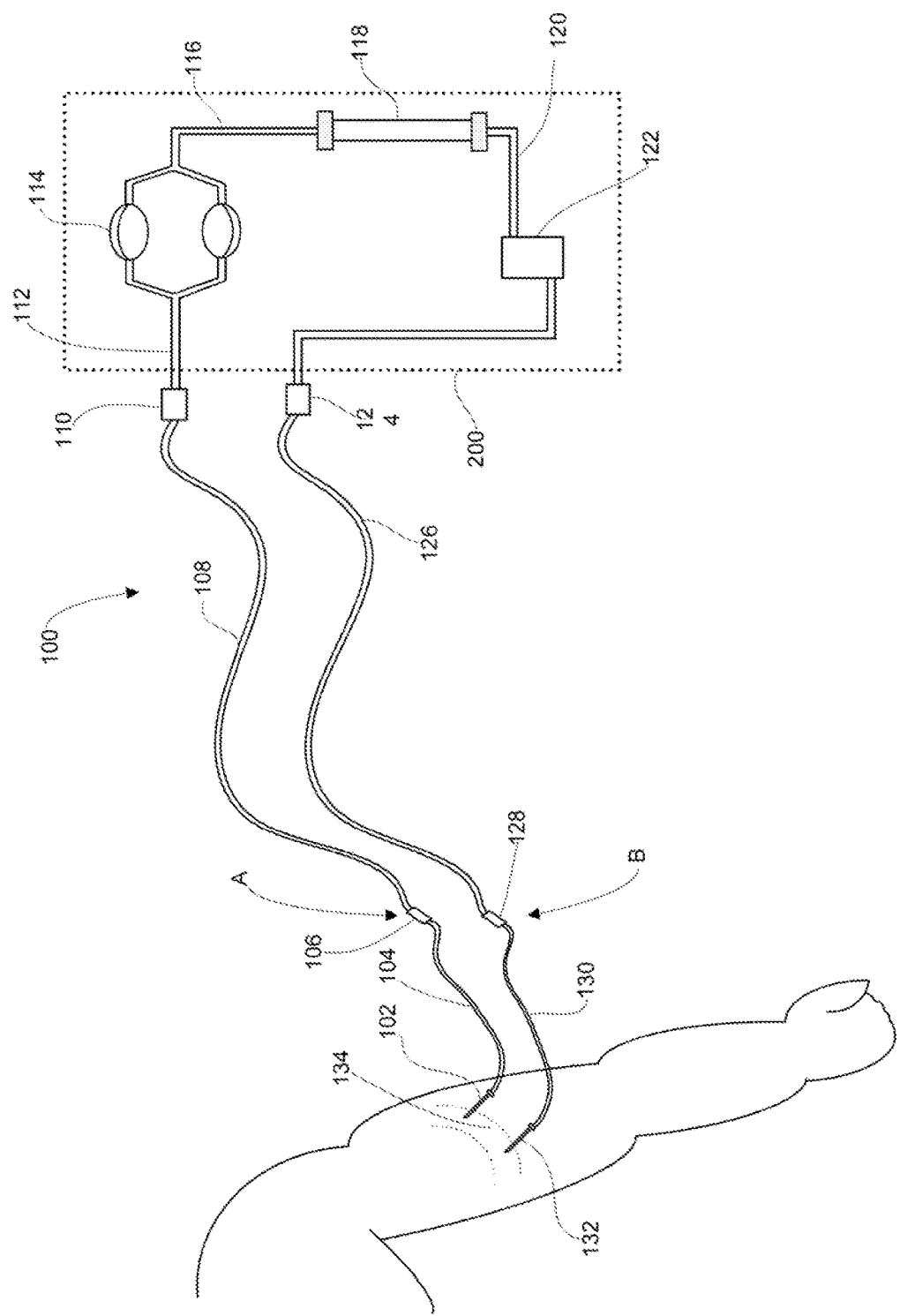
FIG. 4 is a schematic representation of an exemplary blood flow circuit of a hemodialysis system.
Figure 13:
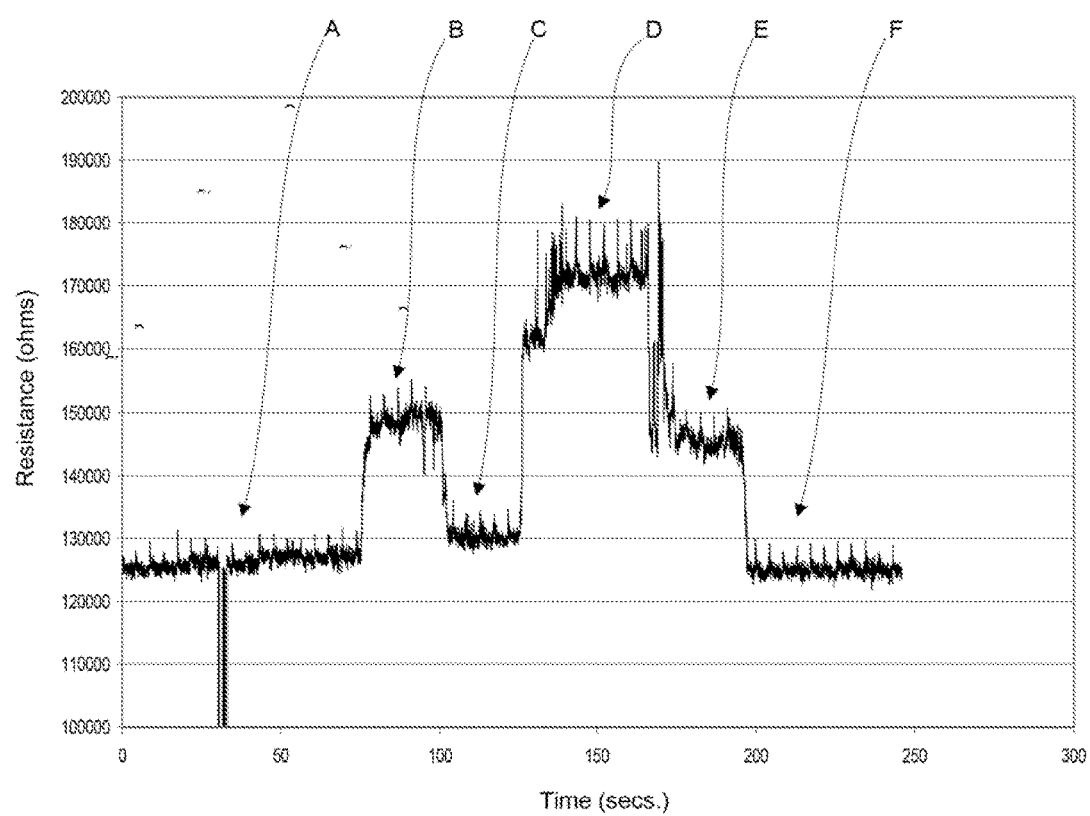
FIG. 13 is a representative plot of the resistance measured by the conductivity circuit of FIG. 1 under various conditions.

FIG. 13 shows test results utilizing the disconnect detection circuit described above and shown in FIG. 1. In this case, a hemodialysis blood circuit and apparatus was employed that is similar to that disclosed in U.S. Patent Application Publication Nos. 2009/0114582 and 2010/0056975, (the contents of which are hereby incorporated by reference). The extracorporeal circuit 210 shown in FIG. 11, comprises a blood pump 114, dialyzer 118, air trap 122, venous blood circuit tubing 126, and arterial blood circuit tubing 108. Extracorporeal circuit 210 mates to a hemodialysis apparatus 220 similar to the one shown in FIG. 12. The blood flow circuit tested included a pair of membrane-based blood pumps arranged on a blood pump cassette 114 shown in FIG. 11, a dialyzer 118, a venous return air trap 122, an arterial blood tubing set 108, a venous blood tubing set 126, arterial and venous connectors 106 and 128, and catheter tubing sets 104, 130 connected to vascular access needles 102, 132 as shown in FIG. 4. The needles 102, 132 were placed in a container holding anticoagulated bovine blood. The blood tubing set 108 and 126 was approximately six feet long, and the catheter tubing sets 104 and 130 were approximately two feet long or less. The needles were alternately manually placed in or withdrawn from the container during blood flow to simulate disconnection of a needle from a fistula or blood vessel. Periods A, C and F in FIG. 13 represent the times during which the needles were submerged in the blood in the container. The electrical resistance measured by the disconnect detection circuit shown in FIG. 1 during these periods averaged between 120,000 and 130,000 ohms. Periods B and E in FIG. 13 represent the times during which the venous return needle 132 (under positive pressure from the blood pumps) was withdrawn several centimeters above the surface of the blood within the container, forming a stream of blood mixed with air as the blood exited the venous return needle and entered the container of blood below. The electrical resistance measured during these periods averaged between 140,000 and 150,000 ohms. Period D represents the time during which one of the needles was completely removed from the container, creating a fully open electrical circuit. The electrical resistance measured during this period averaged between about 160,000 and 180,000 ohms. Thus a controller can be readily programmed to distinguish the difference in the monitored resistance of the electrical circuit between an uninterrupted and an interrupted flow of blood. These results showed that an interruption of the continuity of the blood between the arterial 102 and venous 132 needles can reliably produce a detectable change in the measured electrical resistance between two electrodes when placed relatively closer to the arterial and venous access sites than to the blood processing components 114, 118 and 122 of the extracorporeal blood circuit. Furthermore, even a partial interruption of the continuity of blood flow (as in the streaming of blood through air) can be reliably detected, albeit with a smaller change in the measured electrical resistance.

The invention claimed is:

1. A system for detecting the disconnection of a vascular access device from a blood vessel or vascular graft, comprising:
    a fluid delivery device for pumping fluid through a first tube connected to a first catheter in a first site of the blood vessel or graft, and for receiving fluid through a second tube connected to a second catheter in a second site of the blood vessel or graft;
    a first connector configured to connect the first tube to the first catheter, and a second connector configured to connect the second tube to the second catheter, the first connector having a first electrode in fluid communication with a lumen of said first connector, and the second connector having a second electrode in fluid communication with a lumen of said second connector;
    each said first and second electrodes electrically connected to respective first and second terminals of an electronic circuit;
    the electronic circuit configured to deliver electrical signals to the first and second terminals in order to measure an electrical resistance of a fluid in a fluid path extending from the lumen of the first connector, through the blood vessel or vascular graft, to the lumen of the second connector;
    the electronic circuit comprising:
    a switching network coupled by a capacitor to each of the first and second terminals and configured to provide the electrical signals to the first and second terminals in alternating first and second switch configurations;
    a known reference resistance interposed between the capacitor for the first terminal and the switching network; and
    a voltage measuring circuit configured to measure a sense voltage between the capacitor of the first terminal and the known reference resistance;
    wherein the electronic circuit is configured to determine the electrical resistance of the fluid based on a value of the reference resistance, a measured sense voltage for the first switch configuration and a measured sense voltage for the second switch configuration.

2. The system of claim 1, wherein each said first and second electrode is electrically connected to a corresponding one of the first and second terminals of the electronic circuit through a wire located in a second lumen of a double lumen tube, a first lumen of said double lumen tube configured to carry blood between the fluid delivery device and the first or second catheter.

3. The system of claim 1, wherein the first and second tubes are longer than the first and second catheters.

4. The system of claim 1, wherein the electrical signal corresponding to the first switch configuration is a first reference voltage and the electrical signal corresponding to the second switch configuration is a second reference voltage lower than the first reference voltage.

5. The system of claim 4, further comprising a voltage divider that creates the first and second reference voltages.

6. The system of claim 5, wherein the voltage divider is provided with a main reference voltage Vref from which the voltage divider creates the first and second reference voltages.

7. The system of claim 6, wherein the first reference voltage is close to the main reference voltage Vref and the second reference voltage is close to a ground reference voltage.

8. The system of claim 1, wherein the voltage measuring circuit is arranged to measure the sense voltage before and after each time the switching network changes between the first and second switch configurations, and to determine a change in sense voltage as a difference between the sense voltage measured before and after each time the switching network changes between the first and second switch configurations.

* * * * *